US006399571B1

(12) United States Patent
Gray et al.

(10) Patent No.: US 6,399,571 B1
(45) Date of Patent: *Jun. 4, 2002

(54) CHITINASE CHITIN-BINDING FRAGMENTS

(75) Inventors: Patrick W. Gray, Seattle; Larry W. Tjoelker, Kirkland, both of WA (US)

(73) Assignee: ICOS Corporation, Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/267,574

(22) Filed: Mar. 12, 1999

Related U.S. Application Data

(63) Continuation-in-part of application No. 09/039,198, filed on Mar. 12, 1998, now Pat. No. 6,200,951.

(51) Int. Cl.$^7$ .................. A61K 38/47; A61K 38/16; C07K 19/00; C12N 9/42
(52) U.S. Cl. .................. 514/12; 435/209; 530/350; 424/94.61
(58) Field of Search .................. 435/209; 530/350; 514/12; 424/94.61

(56) References Cited

U.S. PATENT DOCUMENTS

| | | | |
|---|---|---|---|
| 5,258,502 A | 11/1993 | Kuranda et al. | 530/350 |
| 5,326,561 A | 7/1994 | Harman et al. | 424/94.61 |
| 5,433,947 A | 7/1995 | Harman et al. | 424/94.61 |

(List continued on next page.)

FOREIGN PATENT DOCUMENTS

| | | |
|---|---|---|
| WO | WO 91/09955 | 7/1991 |
| WO | WO 92/20808 | 11/1992 |
| WO | WO 94/12650 | 6/1994 |

(List continued on next page.)

OTHER PUBLICATIONS

Altschul et al., "Basic Local Alignment Search Tool," *J. Mol. Biol.*, 215:403–410 (1990).
Andriole et al., "Animal Models: Usefulness for Studies of Fungal Pathogenesis and Drug Efficacy in Aspergillosis," *Clin. Infect. Dis.*, 14(Suppl 1):S134–S138 (1992).
Argueso et al., "Effect of the Enzymes Chitinase and Neuraminidase on the Structure of Human Ocular Mucus," *Investigative Ophthalmology & Visual Science*, 36(4):S997 (Mar. 15, 1995) (Abstract 4615–596).
Bayer et al., "Experimental Intraabdominal Candidiasis in Rabbits: Therapy with Low–Total–Dose Intravenous Amphotericin B," *Antimicrobial Agents Chemotherapy*, 19(1):179–184 (Jan., 1981).
Berger et al., "Secreted placental alkaline phosphatase: a powerful new quantitative indicator of gene expression in eukaryotic cells" *Gene* 66:1–10 (1988).

Bitter et al., "Secretion of Foreign Proteins from *Saccharomyces cerevisiae* Directed by α–Factor Gene Fusions," *Proc. Natl. Acad. Sci. USA*, 81:5330–5334 (1984).
Boot et al., "Cloning of cDNA Encoding Chitotriosidase, Human Chitinase Produced by Macrophage," *J. Biol. Chem.*, 270(44):26252–26256 (Nov. 3, 1995).
Brake et al., "α–Factor–directed synthesis and secretion of mature foreign proteins in *Saccharomyces cerevisiae*" *Proc. Natl. Acad. Sci.* 81:4642–4646 (1984).
Capecchi, "Altering the Genome by Homologous Recombination," *Science*, 244:1288–1292 (1989).
Chilvers et al., "Bronchoalveolar lavage in an immunosuppressed rabbit model of invasive pulmonary aspergillosis," *Mycopathologia*, 108:163–71 (1989).
Chong et al., "Single–column purification of free recombinant proteins using a self–cleavable affinity tag derived from a protein splicing element" *Gene*, 192:271–281 (1997).
Clark–Lewis et al., "Automated Chemical Synthesis of a Protein Growth Factor for Hemopoietic Cells, Interleukin–3," *Science*, 231:134–139 (Jan. 10, 1986).
Clark–Lewis et al., "Structure–Activity Relationships of Interleukin–8 Determined Using Chemically Synthesized Analogs," *J. Biol Chem.*, 266:23128–23134 (1991).
Clarke et al., "The nucleotide sequence of the araC regulatory gene in *Salmonella typhimurim* LT2," *Gene 18*:157–163 (1982).
Davies et al., "Mycolase, a new kind of systemic antimycotic," *Nature 273*:235–236 (May 1978).
Dawson et al., "Synthesis of Proteins by Native Chemical Ligation," *Science*, 266:776–779 (Nov. 4, 1994).
Denning et al., "Efficacy of Cilofungin Alone and in Combination with Amphotericin B in a Murine Model of Disseminated Aspergillosis," *Antimicrobial Agents Chemotherapy*, 35(7):1329–1333 (Jul. 1991).
DeSouza et al., "An Estrogen–Dependent Secretory Protein, which Shares Identity with Chitinases, Is Expressed in a Temporally and Regionally Specific Manner in the Sheep Oviduct at the Time of Fertilization and Embryo Development," *Endocrinology*, 136:2485–2496 (1995).
Escott et al., "Chitinase Activity in Human Serum and Leukocytes," *Infect. Immun.*, 63(12):4770–4773 (Dec., 1995).

(List continued on next page.)

*Primary Examiner*—Rebecca E. Prouty
(74) *Attorney, Agent, or Firm*—Marshall, Gerstein, & Borun.

(57) ABSTRACT

The present invention provides chitin-binding fragments of human chitinase, fragment analogs, purified and isolated polynucleotide sequences encoding such fragments and analogs, and materials and methods for the recombinant production of human chitinase fragment products which are expected to be useful as in products for detecting chitin, binding chitin, and treating fungal infections or for development of products useful for treating the same.

24 Claims, No Drawings

U.S. PATENT DOCUMENTS

| | | | |
|---|---|---|---|
| 5,496,934 A | 3/1996 | Shoseyov et al. | 536/23.7 |
| 5,587,292 A | 12/1996 | Laine et al. | 435/7.9 |
| 6,303,118 B1 | 10/2001 | Aerts | 424/94.61 |

FOREIGN PATENT DOCUMENTS

| | | |
|---|---|---|
| WO | WO 95/34678 | 12/1995 |
| WO | WO 96/40940 | 12/1996 |
| WO | WO 97/36917 | 10/1997 |
| WO | WO 97/47752 | 12/1997 |

U.S. PATENT DOCUMENTS

Falcone et al., "Analysis of a 1.6–μm Circular Plasmid from the Yeast *Kluyveromyces drosophilarum:* Structure and Molecular Dimorphism," *Plasmid,* 15:248–252 (1986).

Feldmann et al., "Rheumatoid Arthritis," *Cell,* 85:307–310 (May 3, 1996).

Flanagan et al., "The kit Ligand: A Cell Surface Molecule Altered in Steel Mutant Fibroblasts" *Cell,* 63:185–194 (1990).

Genbank report for Accession No. U10422. (Jan. 1995).

Genbank report for accession No. X77111. (Jun. 1994).

Genbank report for Accession No. Z36295 (Feb. 1995).

Genbank report for accession No. U14639. (Apr. 1996).

Genbank report for Accession No. M94584. (Jun. 1992).

George et al., "Combination Therapy in Experimental Invasive Aspergillosis," *J. Infect. Dis.,* 168:692–698 (1993).

Georgopapadakou et al., "The Fungal Cell Wall As a Drug Target," *Trends in Microbiology,* 3(3):98–104 (Mar., 1995).

Gillis et al., "Production of Recombinant Human Colony Stimulating Factors in Yeast," *Behring Inst. Mitt.,* No. 83:1–7 (1988).

Hakala et al., "Human Cartilage gp–39, A Major Secretory Product of Articular Chondrocytes and Synovial Cells, Is a Mammalian Member of a Chitinase Protein Family,"*J. Biol. Chem.,* 268(34):25803–25810 (Dec. 5, 1993).

Heitz et al., "Molecular Characterization of a Novel Tobacco Pathogenesis–Related (PR) Protein: A New Plant Chitinase/Lysozyme," *Mol. Gen. Genet.,* 245:256–254 (1994).

Henrissat et al., "New families in the classification of glycosyl hydrolases based on amino acid sequence similarities," *Biochem. J.,* 293:781–788 (1993).

Hollak et al., "Marked Elevation of Plasma Chitotriosidase Activity: A Novel Hallmark of Gaucher Disease," *J. Clin. Invest.,* 93:1288–1292 (Mar., 1994).

Ito et al., "Transformation of Intact Yeast Cells Treated with Alkali Cations" *J. Bacteriol.* 153:163–168 (1983).

Jain et al., "Electroretinograms in early fungal endophthalmitis," *Doc. Ophthalmol.,*69:277–235 (1988).

Johansen et al., "Serum YKL–40: A New Potential Marker of Prognosis and Location of Metastases of Patients With Recurrent Breast Cancer," *Eur. J. Cancer,* 31A(9):1437–1442 (1995).

Jones et al., "Isolation and Characterization of Genes Encoding Two Chitinase Enzymes from *Serratia marcescens,"* *EMBO J.,* 5(3):467–473 (1986).

Kinsman et al., "Antifungal Properties in a Novel Series of Triazino [5,6–b] Indoles," *Antimicrobial Agents Chemotherapy,* 37(6):1243–1246 (Jun., 1993).

Krishnan et al., "Isolation, Cloning, and Characterization of New Chitinase Stored in Active Form in Chitin–lined Venom Reservoir," *J. Biol. Chem.,* 269(33):20971–20976 (Aug. 19, 1994).

Kurjan and Herskowitz, "Structure of a Yeast Pheromone Gene (MFα): A Putative α–Factor Precursor Contains Four Tandem Copies of Mature α–Factor," *Cell,* 30:933–943 (1982).

Lin et al., "The araBAD operon of *Salmonella typhimurium* LT2 II. Nucleotide sequence of araA and primary structure of its product, L–arabinose isomerase," *Gene 34*:123–128 (1985).

Longman et al., "Efficacy of Fluconazole in Prophylaxis and Treatment of Experimental Candida Endocarditis," *Rev. Infect. Dis.,* 12(Suppl. 3): S294–298 (1990).

Louie et al., "Tumor Necrosis Factor Alpha Has a Protective Role in a Murine Model of Systemic Candidiasis," *Infect. Immun.,* 62(7):2761–2772 (Jul., 1994).

Nakajima et al., "In Vitro and In Vivo Antifungal Activities of DU–6859a, a Fluoroquinolone, in Combination with Amphotericin B and Fluconazole Against Pathogenic Fungi," *Antimicrobial Agents Chemotherapy,* 39(7):1517–1521 (Jul., 1995).

Nilsson et al."Affinity Fusion Strategies for Detection, Purification, and Immobilization of Recombinant Proteins", *Prot. Expr. Purification 11*:1–16 (1997).

Orr–Weaver et al., "Yeast transformation: A model system for the study of recombination," *Proc. Natl. Acad. Sci, USA,* 78:6354–6358 (1981).

Overdijk et al., "Human Serum Contains a Chitinase: Identification of an Enzyme, Formerly Described as 4–Methylumbelliferyl–tetra–N–Acetylchitotetraoside Hydrolase (MU–TACT Hydrolase)," *Glycobiology,* 4(6):797–803 (1994).

Park et al., "Treatment of Exogenous Candida Endophthalmitis in Rabbits with Oral Fluconazole," *Antimicrobial Agents Chemotherapy,* 39(4): 958–963 (Apr., 1995).

Patterson et al., "Efficacy of Itraconazole Solution in a Rabbit Model of Invasive Aspergillosis," *Antimicrobial Agents Chemotherapy,* 37(11):2307–2310 (Nov., 1993).

Price et al., "Expression, Purification and Characterization of Recombinant Murine Granulocyte–Macrophage Colony––Stimulating Factor and Bovine Interleukin–2 From Yeast," *Gene,* 55:287–293 (1987).

Recklies et al., "Expression of a Chitinase–like Protein (C–GP39) in Human Articular Cartilage and Synovium," *Arthritis Rheumatism,* 36(9 Suppl.): S190 (1993) (Abstract C15).

Renkema et al., "Synthesis, sorting, and processing into distinct isoforms of human macrophage chitotriosidase," *Eur. J. Biochem.,* 244(2):279–285 (1997).

Renkema et al., "Purification and Characterization of Human Chitotriosidase, a Novel Member of the Chitinase Family of Proteins," *J. Biol. Chem.,* 270(5):2198–2202 (Feb. 3, 1995).

Rose and Broach, "Propagation and Expression of Cloned Genes in Yeast: 2–μm Circle–Based Vectors," *Meth. Enz.,* 185:234–279, D. Goeddel, ed., Academic Press, Inc., San Diego, CA (1990).

Rouse et al., "Efficacy of Cilofungin Therapy Administered by Continuous Intravenous Infusion for Experimental Disseminated Candidiasis in Rabbits," *Antimicrobial Agents Chemotherapy,* 36(1):56–58 (Jan., 1992).

Selitrennikoff, C., "Use of Temperature–Sensitive, Protoplast–Forming *Neurospora crassa* Strain for the Detection of Antifungal Antibiotics," *Antimicrobial Agents Chemotherapy,* 23(5):757–765 (May 1983).

Semino et al., "Homologs of the Xenopus Developmental Gene DG42 are Present in Zebrafish and Mouse and are Involved in the Synthesis of Nod–like Chitin Oligosaccharides During Early Embryogenesis," *Proc. Nat'l. Acad. Sci., USA,* 93:4548–4553 (May, 1996).

Sleep et al., "The Secretion of Human Serum Albumin from the Yeast *Saccharomyces Cerevisiae* Using Five Different Leader Sequences," *Bio/Technol.,* 8:42–46 (1990).

Sleep et al., "*Saccharomyces Cerevisiae* Strains that Overexpress Heterologous Proteins" *Biotechnology* 9:183–187 (1991).

Spitz, "Single–Shot" Intrasplenic Immunization for the Production of Monoclonal Antibodies, *Methods Enz.,* 121:33–41 (1986).

Stearns et al., "Manipulating Yeast Genome Using Plasmid Vectors," *Meth. Enz.,* 185:280–297, Goeddel et al., (ed), Academic Press, Inc., San Diego, CA,. (1990).

Stevens, D., "Animal Models in the Evaluation of Antifungal Drugs," *J. Mycol. Med.,* 6 (Suppl. I):7–10 (1996).

Tjoelker et al., "Anti–inflammatory Properties of a Platelet–activating Factor Acetylhydrolase," *Nature,* 374:549–553 (1995).

Tonnetti et al., "Interleukin–4 and –10 Exacerbate Candidiasis in Mice," *Eur. J. Immunol.,* 25:1559–1565 (1995).

Varki, A., "Does DG42 Synthesize Hyaluronan or Chitin?:A Controversy About Oligosaccharides in Vertebrate Development," *Proc. Nat'l. Acad. Sci., USA,* 93:4523–4525 (May, 1996).

Witt et al., "Comparison of Fluconazole and Amphotericin B for Prevention and Treatment of Experimental Candida Endocarditis," *Amtimicrobial Agents Chemotherapy,* 35(12):2481–2485 (Dec., 1991).

Beitema, J.J., "Structural features of plant chitinases and chitin–binding proteins," *FEBS Letters,* 350:159–163 (1994).

Raikhel et al., "Structure and Function of Chitin–Binding Proteins," *Annu. Rev. Plant Physiol. Plant Mol. Biol.,* 44:591–615 (1993).

Renkema et al., "Chitotriosidase, a chitinase, and the 39–kDa human cartilage glycoprotein, a chitin–binding lectin, are homologues of family 18 glycosyl hydrolases secreted by human macrophages," *Eur. J. Biochem.,* 251:504–509 (Jan., 1998).

Sekine et al., "Characterization of Monoclonal Antibodies to Chitinase A1 and Enhancement of Chitinase A1 Activity by Monoclonal Antibodies," *Biochemical and Biophysical Research Communications,* 204(1):7–16 (Oct., 1994).

CHITINASE CHITIN-BINDING FRAGMENTS

This application is a continuation-in-part of U.S. Ser. No. 09/039,198 filed Mar. 12, 1998, now U.S. Pat. No. 6,200,951.

FIELD OF THE INVENTION

The present invention relates generally to materials comprising chitin-binding fragments of human chitinase enzyme and analogs of the fragments. More particularly, the invention relates to novel purified and isolated polynucleotides encoding such fragment products, to the chitinase fragment products encoded by such polynucleotides, to materials and methods for the recombinant production of such chitinase fragment products and to therapeutic and diagnostic uses of such chitinase fragment products.

BACKGROUND

Chitin is a linear homopolymer of β-(1,4)-linked N-acetylglucosamine residues. This polysaccharide is second only to cellulose as the most abundant organic substance. The exoskeleton of arthropods is composed of chitin. In addition, fungi and other parasites contain chitin in their outer cell wall, where it serves important structural and protective roles. Disruption of the fungal cell wall and membrane has been a useful therapeutic strategy against fungi and parasites. For example, Amphotericin B and fluconazole exert their anti-fungal activity by affecting membrane steroids. Despite the existence of anti-fungal therapeutics, fungal infections of humans have increasingly become responsible for life-threatening disorders. See, Georgopapadakou et al., *Trends Microbiol.*, 3:98–104 (1995). The fungal species and parasites responsible for these diseases are mainly Candida, Aspergillus, Cryptococcus, Histoplasma, Coccidioides and Pneumocystis. These pathogens are particularly dangerous in immunocompromised individuals, such as patients with AIDS, patients undergoing chemotherapy, and immunosuppressed organ transplant patients.

Chitin can be degraded by the enzyme chitinase. Chitinase enzymes are found in plants, microorganisms, and animals. Bacterial chitinase helps to provide a carbon source for bacterial growth. Insects produce chitinase to digest their cuticle at each molt. In plants, chitinase is thought to provide a protective role against parasitic fungi. Chitinases have been cloned from numerous bacterial [e.g., *Serratia marcescens*, Jones et al., *EMBO J.*, 5:467–473 (1986)], plant [e.g., tobacco, Heitz et al., *Mol. Gen. Genet.*, 245:246–254 (1994)], and insect [e.g., wasp, Krishnan et al., *J. Biol. Chem.*, 269:20971–20976 (1994)] species and have been categorieed into two distinct families, designated family 18 and family 19, based on sequence similarities [Henrissat and Bairoch, *Biochem, J.* 293:781–788 (1993)]. Although the catalytic region of the enzymes in family 18 is largely conserved across numerous species, there is very limited sequence similarity across species for the chitin-binding domain. The only feature common to several family 18 chitin-binding domains is the presence of multiple cysteine residues.

Several proteins with low homology to bacterial, insect, and plant chitinases (less than 40% amino acid identity) have been identified in mammals, such as human cartilage gp-39 (C-gp39) [Hakala et al., *J. Biol. Chem.*, 268:25803–25810 (1993)], human glycoprotein YKL-40 [Johansen et al., *Eur. J. Cancer*, 31A:1437–1442 (1995)], oviduct-specific, estrogen-induced protein from sheep [DeSouza et al., *Endocrinology*, 136:2485–2496 (1995)], cows and humans; and a secretory protein from activated mouse macrophages [Chang et al., Genbank M94584]. However, chitin-degrading activity has not been reported for these proteins. The function of these proteins is not known, but they have been postulated to be involved in tissue remodeling. Hakala et al., supra, report that C-gp39 is detectable in synovial and cartilage specimens from rheumatoid arthritis patients, but not from normal humans. Recklies et al., *Arthritis Rheumatism*, 36(9 SUPPL.):S190 (1993) report locaization of the C-gp39 protein to a distinct population of cells in the superficial layers of cartilage. Johansen et al., supra, report that measurements of YKL-40 serum levels are of value as a potential prognostic marker for the extent of metastatic disease and survival of patients with recurrent breast cancer.

Escott et al., *Infect. Immun.*, 63:4770–4773 (1995) demonstrated chitinase enzymatic activity in human leukocytes and in human serum. Overdijk et al., *Glycobiology*, 4:797–803 (1994) described isolation of a chitinase (4-methylumbelliferyl-tetra-N-acetylchitotetraoside hydrolase) from human serum and rat liver. Renkema et al., *J. Biol. Chem.*, 270:2198–2202 (February 1995) prepared a human chitotriosidase from the spleen of a Gaucher disease patient. Their preparation exhibited chitinase activity and the article reports a small amount of amino acid sequence of the protein component of the preparation (22 amino terminal residues and 21 residues of a tryptic fragment). The function of human chitinase is also unknown, but a relationship with the pathophysiology of Gaucher disease is proposed in the article. A later publication by the same group [Boot et al., *J. Biol. Chem.*, 270(44):26252–26256 (November 1995)] describes the cloning of a human macrophage cDNA encoding a product that exhibits chitinase activity. The partial amino acid sequence reported by the group in their February 1995 article matches portions of the deduced amino acid sequence of the human macrophage cDNA product. See also International Patent Publication No. WO 96/40940, which reports two distinct human chitotriosidase cDNAs encoding a 50 kD and a 39kD product, both of which were fully enzymatically active. Renkema et al., *Eur. J. Biochem.*, 244:279–285 (1997) reported that human chitinase is initially produced in macrophages as a 50 kD protein that is in part processed into a 39 kD form that accumulates in lysozymes, and also reported that alternative splicing generates a distinct human chitinase mRNA species encoding a 40 kD chitinase. Both the 39 kD and 40 kD isoforms appeared to be C-terminally truncated and displayed full chitinase enzymatic activity but bound chitin poorly.

In view of the increasing incidence of life-threatening fungal infection in immunocompromised individuals, there exists a need in the art to identify new materials and methods useful for diagnosing and treating fungal infections.

SUMMARY OF THE INVENTION

The present invention provides novel purified and isolated polynucleotides (i.e., DNA and RNA, both sense and antisense strands) encoding human chitinase fragments and analogs thereof having chitin-binding activity but lacking chitinase enzymatic activity; methods for the recombinant production of such fragment products; purified and isolated human chitinase polypeptide fragment products; pharmaceutical compositions comprising such fragment products; and diagnostic or therapeutic agents conjugated to such fragment products thereof. Such fragment products and diagnostic or therapeutic agents conjugated thereto are expected to be useful for detecting chitin, binding chitin, and treating fungal infections or for development of products useful for treating fungal infections.

The nucleotide sequence of two human cDNAs encoding presumed allelic variants of human chitinase, and including noncoding 5' and 3' sequences, are set forth in SEQ ID NO: 1 and SEQ ID NO: 3. The human chitinase coding region corresponds to nucleotides 2 to 1399 of SEQ ID NO: 1 or nucleotides 27 to 1424 of SEQ ID NO: 3, and the putative coding sequence of the mature, secreted human chitinase protein without its signal sequence corresponds to nucleotides 65 to 1399 of SEQ ID NO: 1, or nucleotides 90 to 1424 of SEQ ID NO: 3. The amino acid sequences of the polypeptides encoded by the DNA of SEQ ID NOS: 1 and 3 are set forth in SEQ ID NO:2 and SEQ ID NO: 4, respectively. Twenty-one amino-terminal amino acids (positions −21 to −1 of SEQ ID NOS: 2 and 4) comprise a signal peptide that is cleaved to yield the mature human chitinase protein (positions 1 to 445 of SEQ ID NOS: 2 and 4). It has been determined that the seventy-two C-terminal residues of human chitinase are not critical to chitinase enzymatic activity. Example 5 below illustrates production of an N-terminal fragment that lacks the seventy-two C-terminal residues of human chitinase; the introduction of a stop codon after the codon for amino acid 373 resulted in a recombinant chitinase fragment of about 39 kDa that retained similar specific chitinase enzymatic activity when compared with full length recombinant human chitinase. The cloning of human chitinase cDNA and expression thereof, and the biological activities of recombinant human chitinase are described in detail in U.S. application Ser. No. 08/877,599 filed Jun. 16, 1997, which is a continuation-in-part of U.S. application Ser. No. 08/663,618 filed Jun. 14, 1996, both of which are incorporated herein by reference in their entirety.

The present invention is based on the unexpected discovery that substantially all of the chitin-binding activity of human chitinase is contained within the 99 C-terminal amino acid residues of the 445 amino acid enzyme. Specifically provided by the present invention are chitin-binding, chitinase-inactive polypeptide products. Preferred chitinase fragment products comprise a chitin-binding fragment within the 54 C-terminal amino acids of human chitinase, including a fragment consisting of about the 99 C-terminal amino acids of human chitinase (about residues 347 through 445 of SEQ ID NO: 2), a fragment consisting of about the 72 C-terminal amino acids of human chitinase (about residues 374 through 445 of SEQ ID NO: 2), a fragment consisting of about the 54 C-terminal amino acids of human chitinase (about residues 392 through 445 of SEQ ID NO: 2), and a fragment consisting of about the 49 C-terminal amino acids of human chitinase (about residues 397 through 445 of SEQ ID NO: 2). Also provided by the invention are purified, isolated polynucleotides including DNA encoding such polypeptide fragments; vectors comprising such DNAs, particularly expression vectors wherein the DNA is operatively linked to an expression control DNA sequence; host cells stably transformed or transfected with such DNAs in a manner allowing the expression in said host cell of human chitinase fragment products; a method for producing human chitinase polypeptide fragment products comprising culturing such host cells in a nutrient medium and isolating such polypeptides from said host cell or said nutrient medium; purified, isolated polypeptides produced by this method; fusion proteins comprising such polypeptides fused to a heterologous peptide or polypeptide, including an enzyme such as secreted alkaline phosphatase (SEAP); compositions comprising such human polypeptide fragment products; compositions comprising a human chitinase polypeptide fragment product conjugated to an antifungal agent and methods of treating fungal infection by administering such compositions, optionally with co-administration of additional non-chitinase anti-fungal agents; compositions comprising a chitinase polypeptide fragment product conjugated to a detectable label (including radioisotopes, fluorophores, dyes, electron-dense compounds and enzymes), methods for using such compositions to determine the presence or amount of chitin in a sample, comprising the steps of: (a) contacting the sample with a human chitinase polypeptide fragment product conjugated to a detectable label, and (b) determining the amount of labelled fragment product bound to chitin, and corresponding kits for diagnosing the presence of chitin in a sample; monoclonal antibodies that specifically bind a chitin-binding, chitinase-inactive fragment of human chitinase, including antibodies that specifically bind to an epitope within the 54 C-terminal amino acids of human chitinase as set forth in SEQ ID NO:2; and preferred monoclonal antibodies 243Q and 243M, and antibodies that compete with or bind to the same epitope as 243Q and 243M.

Chitinase polypeptide fragment products of the invention include fragments of human chitinase or allelic variants thereof that substantially retain chitin-binding activity without retaining substantial chitinase enzymatic activity, analogs of such fragments, and fusion proteins comprising such fragments or analogs. Chitinase polypeptide fragment products are useful in therapeutic and diagnostic applications as described below.

Among the "chitin-binding domain" fragments contemplated by the invention are those represented by amino acid residues X through Y of SEQ ID NO: 2, wherein X is a consecutive integer from 347 through 397 and Y is 445, and portions thereof that retain chitin-binding activity. One preferred fragment consists of the ninety-nine C-terminal amino acids of human chitinase (residues 347 through 445 of SEQ ID NO: 2); this fragment has been shown in Example 7 below to retain 80% of the chitin-binding activity of the mature chitinase. Yet other preferred fragments are the fifty-four C-terminal amino acids of human chitinase (residues 392 through 445 of SEQ ID NO: 2), and the 49 C-terminal amino acids of human chitinase (residues 397 through 445 of SEQ ID NO:2), which have also been shown in Example 7 to retain chitin-binding activity. As illustrated in Example 7, a fusion protein containing the 99 C-terminal amino acids of human chitinase was shown to contain the chitin-binding domain of the protein. The boundaries of the chitin-binding domain were further defined by N-terminal and C-terminal truncation of this 99 amino acid region and determination of the chitin binding activity of fusion proteins comprising these truncates. These truncates included those with an N-terminus commencing at amino acid residue 347, 374, 392, 395, 397, 400 or 409 and with a C-terminus at amino acid residue 431, 443 or 445.

Analogs may comprise chitinase fragment analogs wherein one or more of the specified (i.e., naturally encoded) amino acids is deleted or replaced or wherein one or more nonspecified amino acids are added: (1) without loss of one or more of the biological activities (including chitin-binding activity) or immunological characteristics specific to chitinase; or (2) with specific disablement of a particular biological activity of chitinase. The invention contemplates that conservative amino acid substitutions as known in the art may be made without affecting the biological activity of the fragment.

Preferred DNA sequences of the invention include genomic and cDNA sequences as well as wholly or partially chemically synthesized DNA sequences encoding chitin-binding fragments of human chitinase without chitinase enzymatic activity, analogs thereof, and fusion proteins comprising such fragments or analogs. Among the nucleotide sequences contemplated by the invention are those encoding the amino acid sequences of positions X through Y of SEQ ID NO: 2, wherein X is a consecutive integer from 347 through 392 and Y is 445. Nucleotides 1238 through 1399 of SEQ ID NO: 1 (encoding residues 392 through 445 of SEQ ID NO: 2) are a particularly preferred DNA sequence of the invention. This DNA sequence and other DNA sequences which hybridize to the noncoding strand thereof under standard stringent conditions or which would hybridize but for the redundancy of the genetic code, and which encode chitin-binding fragments of a chitinase, are also contemplated by the invention. Exemplary stringent hybridization conditions are as follows: hybridization at 42° C. in 50% formamide and washing at 60° C. in 0.1×SSC, 0.1% SDS. It is understood by those of skill in the art that variation in these conditions occurs based on the length and GC nucleotide base content of the sequences to be hybridized. Formulas standard in the art are appropriate for determining exact hybridization conditions. See Sambrook et al., 9.47–9.51 in *Molecular Cloning*, Cold Spring Harbor Laboratory Press, Cold Spring Harbor, N.Y. (1989).

Among the uses for the polynucleotides of the present invention are use as a hybridization probe, to identify and isolate non-human genomic DNA and cDNA encoding chitin-binding regions of proteins homologous to human chitinase; and to identify those cells which express chitin-binding portions of such proteins and the biological conditions under which such proteins are expressed.

In another aspect, the invention includes biological replicas (i.e., copies of isolated DNA sequences made in vivo or in vitro) of DNA sequences of the invention. Autonomously replicating recombinant constructions such as plasmid and viral DNA vectors incorporating polynucleotides encoding chitin-binding fragments of human chitinase, including any of the DNAs described above, are provided. Preferred vectors include expression vectors in which the incorporated chitinase fragment-encoding cDNA is operatively linked to an endogenous or heterologous expression control sequence and a transcription terminator. Such expression vectors may further include polypeptide-encoding DNA sequences operably linked to the chitinase fragment-encoding DNA sequences, which vectors may be expressed to yield a fusion protein comprising the polypeptide of interest.

According to another aspect of the invention, procaryotic or eucaryotic host cells are stably transformed or transfected with polynucleotide sequences of the invention in a manner allowing the desired chitinase product to be expressed therein. Host cells expressing chitinase fragment products can serve a variety of useful purposes. Such cells constitute a valuable source of immunogen for the development of antibody substances specifically immunoreactive with chitinase. Host cells of the invention are useful in methods for the large scale production of chitinase fragment products wherein the cells are grown in a suitable culture medium and the desired polypeptide products are isolated, e.g., by immunoaffinity purification, from the cells or from the medium in which the cells are grown.

Knowledge of DNA sequences encoding the chitin-binding portion of human chitinase allows for modification of cells to permit or increase expression of the chitin-binding portions. Cells can be modified, (e.g., by homologous recombination) to provide increased expression of the chitin-binding portion of human chitinase by inserting all or part of a heterologous promoter in the appropriate position within the gene. The heterologous promoter is inserted in such a manner that it is operably linked to the DNA sequence encoding the chitin-binding portion of human chitinase. See, for example, PCT International Publication Nos. WO 94/12650, WO 92/20808 and WO 91/09955. Amplifiable marker DNA and/or intron DNA may be inserted along with the heterologous promoter DNA.

Chitinase fragment products may be obtained as isolates from natural cell sources or may be chemically synthesized, but are preferably produced by recombinant procedures involving procaryotic or eucaryotic host cells of the invention. The use of mammalian host cells is also expected to provide for post-translational modifications (e.g., myristolation, glycosylation, truncation, lipidation and tyrosine, serine or threonine phosphorylation) as may be needed to confer optimal biological activity on recombinant expression products of the invention.

The invention further comprehends use of chitinase fragment products in screening for proteins or other molecules (e.g., small molecules) that specifically bind to the chitin-binding domain of human chitinase or that modulate binding of human chitinase to chitin or to human extracellular matrix proteins such as hyaluronic acid. Proteins or other molecules (e.g., small molecules) which specifically bind to chitinase can be identified using fragments of chitinase isolated from plasma, recombinant chitinase fragment products, or cells expressing such products. Proteins or other molecules that bind to the chitin-binding domain of chitinase may be used to modulate its activity. Binding proteins that specifically bind to the chitin-binding domain of chitinase are contemplated by the invention and include antibody substances (e.g., monoclonal and polyclonal antibodies, single chain antibodies, chimeric antibodies, humanized antibodies, human antibodies, and CDR-grafted antibodies, including compounds which include CDR sequences which specifically recognize a polypeptide of the invention). By "specifically bind to the chitin-binding domain of chitinase" it is meant that the binding protein recognizes exclusively the chitin-binding domain of chitinase and not the catalytically active portion of chitinase. Binding proteins are useful, in turn, in compositions for immunization as well as for purifying chitinase, and are useful for detection or quantification of chitinase in fluid and tissue samples by known immunological procedures. Anti-idiotypic antibodies specific for chitinase-specific antibody substances are also contemplated.

Antibodies that specifically bind to chitin-binding domain are useful in methods for detecting or quantifying the presence of chitin-binding domain, e.g., in a sandwich ELISA assay, and for detecting or quantifying the presence of yeast or fungi, e.g., by adding a chitin-binding domain which binds to the yeast or fungi, followed by adding a labeled antibody specific for the chitin-binding domain. Detection of chitin-binding domain in human blood (plasma or serum) samples may also be correlated to a diagnostic standard indicative of a disease state involving chitinase, such as Gaucher's disease. Presently preferred antibodies are monoclonal antibodies 243Q and 243M, produced by hybridomas 243Q (Accession No. HB-12688) and 243M (Accession No. HB-12657), respectively, and monoclonal antibodies that compete with or bind to the same epitope recognized by 243Q or 243M.

The scientific value of the information contributed through the disclosures of DNA and amino acid sequences of the present invention is manifest. As one series of examples, knowledge of the sequence of a cDNA for chitinase makes possible the isolation by DNA/DNA hybridization or polymerase chain reaction (PCR) of genomic DNA sequences encoding other mammalian chitinases and the like. DNA/DNA hybridization or PCR procedures carried out with DNA sequences of the invention under conditions of stringency standard in the art are likewise expected to allow the isolation of DNAs encoding human allelic variants of chitinase, other structurally related human proteins sharing the chitin-binding property of chitinase, and the chitin-binding regions of non-human species proteins homologous to chitinase. The DNA sequence information provided by the present invention also makes possible the development, by homologous recombination or "knockout" strategies [see, e.g., Kapecchi, *Science*, 244: 1288–1292 (1989)], of animals that fail to express a functional chitinase enzyme, overexpress chitinase enzyme, or express a variant chitinase enzyme. Such animals are useful as models for studying the in vivo activity of chitinase or modulators of chitinase. Polynucleotides of the invention when suitably labelled are useful in hybridization assays to detect the capacity of cells to synthesize chitinase. Polynucleotides of the invention may also be the basis for diagnostic methods useful for identifying a genetic alteration(s) in the chitinase locus that underlies a disease state or states. Also made available by the invention are anti-sense polynucleotides relevant to regulating expression of chitinase by those cells which ordinarily express the same.

The invention contemplates that chitin-binding fragment products may be fused to a heterologous polypeptide. For example, such products may be fused to a portion of an immunoglobulin, such as the constant region, for therapeutic purposes. As another example, such products may be fused to a polypeptide useful as a detectable label or marker, such as a polypeptide with enzymatic activity or a polypeptide carrying a specifically detectable epitope, such as a myc epitope or FLAG epitope tag (Eastman Kodak).

Chitin-binding fragments may also be fused to another protein of interest to facilitate purification of the protein of interest via affinity binding to a chitin matrix. The fusion protein may then be obtained by elution from the column, or the protein of interest may be cleaved from the chitin-binding domain followed by elution of the cleaved protein. See Chong et al., *Gene*, 192:271–281 (1997).

The human chitinase fragment products of the invention are also useful as a chitin-specific reagent for specifically identifying the presence of chitin in a sample. According to this aspect of the invention, a chitinase fragment product having chitin-binding activity is conjugated with a detectable label, such as a radioisotope, fluorophore, dye, electron-dense compound, or enzyme, contacted with the sample to be tested, and analyzed qualitatively or quantitatively for the presence of chitin. "Conjugated" as used herein means linked by covalent bonds. Such techniques are well known and illustrated in, e.g., U.S. Pat. No. 5,587,292, incorporated herein by reference. The amount of chitin thus measured can be indicative of the fungal load in an infected patient. Two preferred fragments for use according to this method are the 54 amino acid chitin-binding domain consisting of amino acid residues 392 through 445 of the human chitinase amino acid sequence set out in SEQ ID NO: 2 and the 49 amino acid chitin-binding domain consisting of amino acid residues 397 through 445 of SEQ ID NO: 2.

The invention also provides conjugates comprising chitin-binding chitinase fragments and an imaging agent, such as gamma- and positron-emitting radioisotopes for radionuclear imaging (e.g., 157Gd, 55Mn, 162Dy, 52Cr, 56Fe, 111In, 97Ru, 67Ga, 68Ga, 72As, 89Zr, 201Tl, 99Tn, 90Y); paramagnetic metal chelates, nitroxyl spin labelled compounds or other agents (e.g., Gd(III), Eu(III), Dy(III), Pr(III), Pa(IV), Mn(II), Cr(III), Co(III), Fe(III), Cu(II), Ni(II), Ti(III) and V(IV), GdDTPA/dimeglumine [Magnevist™]) for MRI imaging; contrast enhancement agents for X-ray based imaging, including CT scans (e.g., bromine- or iodine-containing compounds); and other agents known in the art. Such conjugates are expected to bind yeast cell wall chitin and thus to be useful in methods for detecting or localizing yeast in vivo in mammals.

Administration of chitinase fragment products and therapeutic agents comprising such products to mammalian subjects, especially.humans, for the purpose of ameliorating disease states caused by chitin-containing parasites such as fungi is contemplated by the invention. Fungal infections (mycoses) such as candidiasis, aspergillosis, coccidioidomycosis, blastomycosis, paracoccidioidomycosis, histoplasmosis, cryptococcosis, chromoblastomycosis, sporotrichosis, mucormycosis, and the dermatophytoses can manifest as acute or chronic disease. Pathogenic fungi cause serious, often fatal disease in immunocompromised hosts. Cancer patients undergoing chemotherapy, immunosuppressed individuals, and HIV-infected individuals are susceptible to mycoses caused by Candida, Aspergillus, *Pneumocystis carinii*, and other fungi. Amphotericin B and fluconazole are useful therapeutics for fungal infections, but toxicity associated with these drugs causes serious adverse side effects that limit their usefulness. The mortality of systemic candidiasis is greater than 50% despite Amphotericin B treatment. Animal models for fungal infection are illustrated below in Examples 9 through 15 and have been described in the art.

Specifically contemplated by the invention are compositions comprising chitinase fragment products for use in methods for treating a mammal susceptible to or suffering from fungal infections. It is contemplated that the chitinase fragment products may be conjugated to other conventional anti-fungal agents, including amphotericin B and the structurally related compounds nystatin and pimaricin; 5-fluorocytosine; azole derivatives such as fluconazole, ketoconazole, clotrimazole, miconazole, econazole, butoconazole, oxiconazole, sulconazole, terconazole, itraconazole and tioconazole; allylamines-thiocarbamates, such as tolnaftate, naftifme and terbinafme; griseofulvin; ciclopirox olamine; haloprogin; undecylenic acid; and benzoic acid. [See, e.g., Goodman & Gilman, The Pharmacological Basis of Therapeutics, 9th ed., McGraw-Hill, NY (1996).] According to this aspect of the invention, the chitin-binding fragment products serve as a vector to target known fungicidal or fungistatic compounds to pathogenic chitin-bearing fungi, and thus may improve the effectiveness of these conventional anti-fungal agents, perhaps by rendering the fungi more susceptible to their action. A reduction in the amount of conventional anti-fungal agent needed to exert the desired therapeutic effect may allow the drugs to be used at less toxic levels. The ability to selectively target fungi or yeast using a chitin-binding domain fragment also allows administration of such fragments conjugated to cytotoxic agents that are not themselves selectively anti-fungal. This aspect of the invention contemplates conjugation of chitin-binding chitinase fragments to any cytotoxic agent known in the art, including radioisotopes (such as 90Y, 188Re, 186Re, 199Au, 64Cu, 67Cu, 131I), toxins and chemotherapeutic agents, that would be effective against yeast. Suitable cytotoxic agents can be easily identified using methods known in the art. Using human chitinase chitin-binding domain for this purpose is more advantageous than using chitin-binding domains of chitinases of other species because human polypeptides are expected to be non-immunogenic in humans.

Chitin-binding domain fragments themselves may have anti-fungal effects through disruptive cross-linking of yeast cell wall, and may be co-administered alone or in combination with other anti-fungal agents. Multimeric chitin-binding domain fragments, which may be especially useful for this purpose, are contemplated by the invention, including multimeric fragments that have been covalently cross-linked by chemical means and recombinantly produced polypeptides comprising multiple chitin-binding domains linked in tandem. The administration of chitin-binding domain fragments, either monomeric or multimeric, may reduce the amount of co-administered anti-fungal agent necessary to exert a desired therapeutic effect.

Thus, the invention contemplates the use of chitinase fragment products in the preparation of a medicament for the prophylactic or therapeutic treatment of fungal infections.

Therapeutic/pharmaceutical compositions contemplated by the invention include chitinase fragment products, which may be conjugated to another therapeutic agent, and a physiologically acceptable diluent or carrier and may also include other anti-fungal agents. Dosage amounts indicated would be sufficient to supplement endogenous chitinase activity. For general dosage considerations see *Remington: The Science and Practice of Pharmacy*, 19th ed., Mack Publishing Co., Easton, Pa. (1995). Dosages will vary between about 1 µg/kg to 100 mg/kg body weight, and preferably between about 0.1 to about 20 mg chitinase/kg body weight. Therapeutic compositions of the invention may be administered by various routes depending on the infection to be treated, including via subcutaneous, intramuscular, intravenous, intrapulmonary, transdermal, intrathecal, topical, oral, or suppository administration.

The invention also contemplates that the overexpression of chitinase in Gaucher disease or at sites of inflammation (such as in rheumatoid arthritis) may have deleterious effects on the extracellular matrix and, in such disease settings, inhibitors of chitinase activity, including chitinase fragment products themselves or inhibitors of chitin-binding identified by the screening methods described above, may provide therapeutic benefit, e.g. by reducing remodeling or destruction of the extracellular matrix.

The human chitinase cDNA has been isolated from a macrophage cDNA library. Macrophages are known to be closely associated with rheumatoid arthritis lesions [Feldman et al., *Cell*, 85:307–310 (1996)], and macrophage products such as TNP-α are implicated in disease progression. A protein with homology to human chitinase, C-gp39, has been detected in the synovium and cartilage of rheumatoid arthritis patients. While the natural substrate for human chitinase is probably chitin from pathogenic organisms, the enzyme may also exhibit activity on endogenous macromolecules which form the natural extracellular matrix. For example, it has been suggested that hyaluronic acid, a major component of the extracellular matrix, contains a core of chitin oligomers. [Semino et al., *Proc. Nat'l Acad. Sci.*, 93:4548–4553 (1996); Varki, *Proc. Nat'l. Acad. Sci.*, 93:4523–4525 (1996).] Chitinase may therefore be involved in degradation of extracellular matrix in diseases such as rheumatoid arthritis. The role of chitinase may be determined by measuring chitinase levels and/or the effects of chitinase administration or chitinase inhibition in synovial fluid isolated from arthritic joints. Endogenous chitinase levels can be measured by enzymatic assay or with an antibody. Viscosity of synovial fluid can be measured before and after chitinase treatment; a decrease of viscosity associated with chitinase would be consistent with an endogenous chitinase substrate. Modulation of chitinase activity could thereby modulate the progression of joint destruction in rheumatoid arthritis.

Also contemplated by the invention are methods for screening for inhibitors of chitinase activity, which may be useful in the manner described in the preceding paragraph. A method for screening samples to identify agents that inhibit chitinase is reported in, e.g., WO 95/34678 published Dec. 21, 1995.

DETAILED DESCRIPTION OF INVENTION

Other aspects and advantages of the present invention will be understood upon consideration of the following illustrative examples. Example 1 describes the isolation of human chitinase cDNA clones from a human macrophage cDNA library. Example 2 addresses the pattern of chitinase gene expression in various human tissues. Example 3 describes the recombinant expression of the human chitinase gene in prokaryotic cells and purification of the resulting enzyme. Example 4 provides a protocol for the recombinant production of human chitinase in yeast. Example 5 describes the recombinant expression of the human chitinase gene in mammalian cells and purification of the resulting protein. Example 6 describes production of human chitinase polypeptide analogs and fragments by peptide synthesis or recombinant production methods. Example 7 describes production of human chitinase fragments having chitin-binding activity and analogs thereof. Example 8 provides a protocol for generating monoclonal antibodies that are specifically immunoreactive with human chitinase. Example 9 describes an assay for the measurement of chitinase catalytic activity. Example 10 addresses determination of the anti-fungal activity of test drugs in vitro. Example 11 addresses determination of the anti-fungal activity of test drugs in vivo in a mouse model, and Examples 12 through 15 address rabbit models of invasive aspergirosis, disseminated candidiasis, Candida ophthahmitis, and Candida endocarditis. Example 16 compares chitin-binding and chitin hydrolysis activities of full length human chitinase and a C-terminally truncated fragment. Example 17 addresses conjugation of chitin-binding fragments to other moieties.

EXAMPLE 1

Isolation of Chitinase cDNA Clones

A cDNA library was prepared from peripheral blood monocyte-derived macrophages as described in Tjoelker et al., *Nature*, 374:549–552 (1995). Clones from the library were randomly chosen and plasmid DNA was purified from individual clones. The sequence of approximately 300 to 500 bases from the end of DNA from each clone was determined on an automated sequencer (Model 373, Applied Biosystems, Foster City, Calif.) using primer JHSP6, which hybridizes to the plasmid vector pRc/CMV (Invitrogen, San Diego, Calif.) adjacent to the cDNA cloning site:

JHSP6: 5'-GACACTATAGAATAGGGC-3' (SEQ ID NO: 5)

The nucleotide and deduced amino acid sequence of these cDNA clones were compared to sequences in nucleotide and peptide sequence databases to determine similarity to known genes. Sequence comparisons were performed by the BLAST Network Service of the National Center for Biotechnology Information using the alignment algorithm of Altschul et al., *J. Mol. Biol.*, 215:403–410 (1990). Clone MO-911 exhibited significant homology to several different sequences, including mouse macrophage secretory protein YM-1 precursor (Genbank accession no. M94584), human cartilage gp-39 (Hakala et al., supra), oviductal glycoprotein from sheep, cow, and humans (DeSouza et al., supra), and chitinases from parasite (Oncocerca, Genbank accession no. U14639), wasp (Chelonus, Genbank accession no. U10422), plant (Nicotiana, Genbank accession no. X77111), and bacteria (Serratia, Genbank accession no. Z36295); its highest observed homology was to mammalian genes that encoded proteins with chitinase homology but no demonstrated chitinase activity. Further sequence analysis of MO-911 suggested that it contained a portion of the coding region for a human chitinase homolog.

The DNA sequence of clone pMO-218 (deposited on Jun. 7, 1996 under the terms of the Budapest Treaty with the American Type Culture Collection, 12301 Parklawn Drive, Rockville, Md. 20852, U.S.A. under Accession No. 98077) is set forth in SEQ ID NO: 1, and the encoded amino acid sequence is set forth in SEQ ID NO: 2. MO-218 appeared to include the entire coding region of the human chitinase cDNA (nucleotides 2 to 1399 of SEQ ID NO: 1), which comprises a twenty-one amino acid putative signal sequence followed by 445 encoded amino acids (residues 1 to 445 of SEQ ID NO: 2). The twenty-two amino acids following the putative signal sequence exactly match the amino-terminal sequence of purified human chitotriosidase reported in Renkema et al., supra. Renkema et al. also described a twenty-one amino acid sequence from a tryptic fragment of human chitotriosidase which corresponds exactly to residues 157 to 177 of MO-218 (SEQ ID NO: 2). Boot et al., supra, report the cloning of a human chitotriosidase cDNA which contains a coding sequence essentially identical to that of MO-218. The sequence of MO-218 differs from Boot et al. by an additional fourteen nucleotides at the 5' end and by a nucleotide change at nucleotide 330 in the coding region.

To confirm that MO-218 indeed contained the entire coding region of the cDNA, a $^{32}$P-labelled probe P-1 (TGGGATCATCAGCAGGACCATGAAACCTGCCCA GGCCACAGACCGCACC AT, SEQ ID NO: 6) was prepared that corresponded to the complement of nucleotides 2 through 52 of MO-218 (SEQ ID NO: 1). Probe P-1 was designed to hybridize with clones that are at least as long as MO-218 at the 5' end. The probe was hybridized with a portion (approximately 30,000 clones) of the human macrophage cDNA library described above, in 40% formamide and hybridization buffer (5×SSPE, 10×Denhardt's, 100 µg/ml denatured salmon sperm DNA, and 2% SDS) at 42° C. overnight. The filters were washed and three clones that hybridized were chosen for sequence analysis. The longest clone was designated pMO-13B (deposited on Jun. 7, 1996 under the terms of the Budapest Treaty with the American Type Culture Collection, 12301 Parklawn Drive, Rockville, Md. 20852, U.S.A. under Accession No. 98078). The DNA sequence of pMO-13B is set forth in SEQ ID NO: 3 and the encoded amino acid sequence is set forth in SEQ ID NO: 4. This clone contains 25 additional nucleotides at the 5' end compared with MO-218; in addition, MO-13B (SEQ ID NO: 3) contains one nucleotide substitution at nucleotide 330 (corresponding to nucleotide 305 of MO-218, SEQ ID NO: 1) which changes the encoded amino acid at position 80 of the mature protein from a glycine (in SEQ ID NO: 2) to a serine (in SEQ ID NO: 4).

EXAMPLE 2

Chitinase Gene Expression Pattern in Human Tissues

Northern blot analysis was performed to identify tissues in which the human chitinase is expressed. A multiple human tissue Northern blot (Clontech, Palo Alto, Calif.) was hybridized with the entire coding region of MO-218 under standard stringent conditions (according to the Clontech laboratory manual). Greatest hybridization was observed to lung tissue (+++) and ovary (+++), with much smaller levels (+) in thymus and placenta. The size of the hybridizing mRNA was 2.0 kb for lung, ovary and thymus, which corresponds well with the size of the cloned cDNA (1.6 kb, or about 1.8 kb including the polyA tail). The size of the hybridizing placental mRNA was considerably smaller, at 1.3 kb. Chitinase hybridization was not observed in spleen, prostate, testes, small intestine, colon, peripheral blood leukocytes, heart, brain, liver, skeletal muscle, kidney, or pancreas. Chitinase expression in lung is consistent with a protective role against pathogenic organisms that contain chitin, since the lung represents the primary route of entry for fungal pathogens.

EXAMPLE 3

Production of Recombinant Human Chitinase in Bacterial Cells

The mature coding region of MO-218 was engineered for expression in *E. coli* as a C-terminal truncated analog. PCR was used to generate a DNA fragment for expression using a primer corresponding to nucleotides 65 to 88 of the MO-218 chitinase cDNA preceded by an initiating methionine codon and an XbaI restriction endonuclease site (5'-TACATCTAGAATTATGGCAAAACTGGTCTGCTACTT CACC-3', SEQ ID NO: 7), and a downstream primer encoding nucleotides 1163 to 1183 of MO-218 followed by a stop codon and a HindIII site (5'-AGATCTAACCTTAGGTGCCTGAAGACAAGTATGG-3', SEQ ID NO: 8). The downstream primer contained an adenine at base 25, while the MO-218 sequence contains a guanine at the corresponding nucleotide position. Consequently, the resulting DNA fragment contains a thymine rather than a cytosine at the position corresponding to nucleotide 1172 of the MO-218 sequence, and the encoded chitinase fragment, set forth in SEQ ID NO: 15, is also an analog that contains a serine at mature amino acid position 370 instead of the proline encoded by MO-218. The resulting DNA fragment was digested with XbaI and HindIII and cloned into plasmid pAraBAD (which is also known by the designation pAraCB).

Plasmid pAraCB was prepared as follows. Plasmid pUC19 was modified to include an arabinose promoter and subsequently to include AKAP 79 encoding sequences. The arabinose promoter [Wilcox et al., *Gene*, 34:123–128 (1985); Wilcox, et al., *Gene*, 18:157–163 (1982)] and the araC gene were amplified by PCR from the arabinose operon BAD of *Salmonella typhimurium* as an EcoRI/XbaI fragment with the primers araC-2 (SEQ ID NO: 9) and arab-i (SEQ ID NO: 10):

araC-2 TACAGAATTATTCACATCCGGCCCTG SEQ ID NO: 9 arab-1 TACATCTAGACTCCATCCAGAAAAACAG-GTATGG SEQ ID NO: 10

Primer araC-2 encodes an EcoRI site (underlined) and a termination codon (italics) for the araC gene product. Primer arab-1 encodes a putative ribosome binding domain (italics) and an xbaI restriction site (underlined). PCR with these primers produced a 1.2 kb fragment which was digested with EcoRI and XbaI and subdloned into pUC19 (New England Biolabs, Beverly, Mass.) previously digested with the same two enzymes. The resulting plasmid was designated pAraCB and contained a polylinker region (SEQ ID NO: 11) flanked at the 5' end with a XbaI restriction site (underlined) and at the 3, end with a HindIII site (italics).

araCB polylinker TCTAGAGTCGACCTGCAGGCATG-CAAGCTT SEQ ID NO: 11

Transformants containing the resulting expression plasmid (pAraMO218) were induced with arabinose and grown at 37° C. These transformants produced inclusion bodies containing a 39 kDa protein which was a truncated form of chitinase (engineered to contain 373 instead of 445 amino acids). This chitinase fragment contains four cysteine residues, while the full length chitinase contains ten cysteine residues. The inclusion bodies were separated from the *E. coli* culture and electrophoresed on SDS-PAGE. The 39 kDa band was transferred to a PVDF membrane and amino terminal sequenced. The majority (about two-thirds) of the material contained a sequence corresponding to the amino terminus of human chitinase. The remaining material corresponded to a contaminating *E. coli* protein, porin. This recombinant chitinase preparation from *E. coli* was useful for producing polyclonal and monoclonal antibodies (described below in Example 8).

When transformants containing the Ara-chitinase expression plasmid were grown at 25° C., inclusion bodies were not observed and expression of recombinant product was decreased from about ten percent of total cell protein to about one percent. However, this material produced at 25° C. exhibited chitinase catalytic activity.

EXAMPLE 4

Production of Recombinant Human Chitinase in Yeast Cells

Exemplary protocols for the recombinant expression of human chitinase in yeast and for the purification of the resulting recombinant protein follow. The coding region of human chitinase is engineered into vectors for expression in *Saccharomyces cerevisiae* using either PCR or linker oligonucleotides designed to encode a fusion polypeptide containing a secretion mediating leader to the coding region for human chitinase corresponding to the amino terminus of the natural molecule. Secretion signal peptides include, e.g., SUC2 or equivalent leaders with a functional signal peptidase cleavage site, or pre-pro-alpha factor or other complex leader composed of a pre, or signal peptide, and a pro, or spacer region, exhibiting a KEX2 cleavage site. The DNA encoding the signal sequence can be obtained by oligonucleotide synthesis or by PCR. The DNA encoding the pre-pro-alpha factor leader is obtained by PCR using primers containing nucleotides 1 through 20 of the alpha mating factor gene and a primer complementary to nucleotides 255 through 235 of this gene [Kujan and Herskowitz, *Cell*, 30:933–943 (1982)]. The pre-pro-alpha leader coding sequence and human chitinase coding sequence fragments are ligated into a plasmid containing the yeast alcohol dehydrogenase (ADH2) promoter, such that the promoter directs the expression of a fusion protein. As taught by Rose and Broach, [*Meth. Enz.*, 185:234–279, D. Goeddel, ed., Academic Press, Inc., San Diego, Calif. (1990)], the vector further includes an ADH2 transcription terminator downstream of the cloning site, the yeast "2-micron" replication origin, a selectable marker, for example TRP1, CUP1 or LEU2 (or LEU2-d) or other equivalent gene, the yeast REP1 and REP2 genes, the *E. coli* beta lactamase gene, and an *E. coli* origin of replication. The beta-lactamase and TRP1 genes provide for selection in bacteria and yeast, respectively. The REP1 and REP2 genes encode proteins involved in plasmid copy number replication.

Alternatively, other fusion points within the chitinase coding region may be chosen. Truncates of the coding region may be used to increase homogeneity of the product, increase the specific activity or alter the substrate specificity.

The DNA constructs described in the preceding paragraphs are transformed into yeast cells using a known method, e.g. lithium acetate treatment [Stearns et al., *Meth. Enz.*, supra, pp. 280–297] or by equivalent methods. The ADH2 promoter is induced upon exhaustion of glucose in the growth media [Price et al., *Gene*, 55:287 (1987)]. The pre-pro-alpha sequence or other leader sequence effects secretion of the fusion protein, releasing the mature human chitinase peptide from the cells. The signal peptide leader is processed by signal peptidase or, in the case of pre-pro-alpha removal of the pro region, by the KEX2 protease [Bitter et al., *Proc. Natl. Acad. Sci. USA*, 81:5330–5334 (1984)].

Chitinase contains in its mature amino acid sequence two dibasic sequences at positions 107–108 (Lys-Arg) and 209–210 (Arg-Lys) that may be proteolytically clipped by the KEX2 protease during secretion. To stabilize and/or increase the level of product secreted from cells, these sequences could be mutated to eliminate the potential sites for proteolysis as shown by Gillis et al. [*Behring Inst. Mitt.*, No. 83:1–7 (1988)] or by expressing chitinase without dibasic modifications in a host that is deficient in KEX2. Such hosts can be obtained either by screening for non-KEX2 protease containing mutants, or by manipulation of the genomic KEX2 locus by gene replacement/gene disruption techniques [Orr-Weaver et al., *Proc. Natl. Acad. Sci, USA*, 78:6354–6358 (1981)].

Recombinant chitinase may be secreted from *Saccharomyces cerevisiae* using similar vectors containing alternative promoters PRB1, GAL4, TPI, or other suitably strong promoters bearing fragments or by fusion to a variety of leader sequences [Sleep et al., *Bio/Technol.*, 8:42–46 (1990)].

Other non-*Saccharomyces cerevisiae* suitable expression hosts include *Kluyveromyces lactis, Schizosaccharomyces pombe, Pichia pastoris* and members of the Hansenula or Aspergillus geni. Analogous recombinant expression systems for these fungi include the organism and their appropriate autonomously replicating vector [e.g. Falcone et al., *Plasmid*, 15:248–252 (1988)] or multiply integrated expression cassettes. These systems also rely on signal sequences or leaders of the types described above to mediate secretion into the medium.

The secreted recombinant human chitinase is purified from the yeast growth medium by, e.g., the methods used to purify chitinase from bacterial and mammalian cell supernatants (see Example 3 above and Example 5 below).

Alternatively, the mature form of the recombinant chitinase product may be expressed in the cytoplasms of the *Saccharomyces cerevisiae* cells or analogous host, and purified from the lysed host cells. The protein may be refolded during the act of purification to obtain appropriate levels of specific activity.

EXAMPLE 5

Production of Recombinant Human Chitinase in Mammalian Cells

A. Expression in COS Cells

The MO-218 clone and the MO-13B clone, both of which contain full length human chitinase cDNA 3' to the CMV promoter of pRc/CMV, were isolated. A third plasmid, which corresponded to the same C-terminal fragment expressed in bacterial cells in Example 3 above, was prepared as follows. The MO-218 plasmid was amplified by PCR using oligonucleotide primer 218-1 (CGCAAGCTTGAGAGCTCCGTrCCGCCACATGGTGCGGTGTGTGCC, SEQ ID NO: 12), which contains a Hind III site and nucleotides 2 through 23 of the MO-218 chitinase cDNA of SEQ ID NO: 1, and with complementary downstream primer T-END (GACTCTAGACTAGGTGCCTGAAGGCAAGTATG, SEQ ID NO: 13), which contains nucleotides 1164 through 1183 of MO-218, a stop codon and an XbaI site. The amplified DNA was purified by electrophoresis, digested with XbaI and HindIII, and cloned into the pRc/CMV vector (Invitrogen, San Diego, Calif.) previously cut with the same restriction enzymes. The junctions of the resulting clone was sequenced on a Model 373 (Applied Biosystems, Foster City, Calif.), confirming that the clone encoded the predicted engineered protein sequence, set forth in SEQ ID NO: 14.

All three plasmids were transiently transfected into COS cells by the DEAE transfection method [see, e.g., Sambrook et al., *Molecular Cloning: a Laboratory Manual*, 2d ed., Cold Spring Harbor, N.Y.: Cold Spring Harbor Laboratory (1989).). After three days at 37° C., media from cells was assayed for chitinase activity in vitro as described below in Example 9. Each culture produced significant chitinase activity (600–800 mU/ml/min), and similar amounts were observed for each construct.

Recombinant human chitinase was purified as follows. Five days after transfection of COS cells with the pRc/CMV-MO-13B plasmid, conditioned media from the culture was harvested and diluted with an equal volume of water. The diluted conditioned media was applied to a Q-Sepharose Fast Flow column (Pharmacia Biotech, Uppsala, Sweden) which was pre-equilibrated in 25 mM Tris, 10 mM sodium chloride, 1 mM EDTA, at pH 8.0. Approximately 95% of the chitinase activity flowed through and did not bind to the column. This Q-Sepharose flow through was adjusted to 1.2 M ammonium sulfate and applied to a Butyl-Sepharose 4 Fast Flow column (Pharmacia) which was pre-equilibrated in 25 mM Tris, 1.2 M ammonium sulfate, 1 mM EDTA, at pH 8.0. Protein was eluted using a reverse gradient of 1.2 M to 0 M ammonium sulfate in 25 mM Tris, pH 8.0. A single absorbance peak at 280 nm corresponding to the chitinase activity peak was eluted at low salt. This material was greater than 85% pure as determined by SDS-PAGE and contained approximately 60% of the chitinase activity. The protein was then concentrated and buffer exchanged into 20 mM Tris, 150 mM sodium chloride, at pH 8.0 using a 10,000 MWCO membrane (Ultrafree™ 10K, Millipore Corp., Bedford, Mass.). This preparation was then tested for enzymatic and anti-fungal activity in vitro as described in Examples 9 and 10 below. The recombinant preparation had a chitotriosidase activity of 90 nmol/min per mg protein.

B. Expression in CHO Cells

The chitinase gene was inserted into pDEF1 (the construction of which is described in Example 4 of U.S. application Ser. No. 08/847,218 filed May 1, 1997, incorporated herein by reference) by excising the 1.77 kb HindIII/XbaI fragment containing the full length chitinase gene from pRc/CMV/MO-13B and ligating the fragment with HindIII/XbaI-digested pDEF1, to create plasmid pDEF1/CTN.1. The 1.77 kb HindIII/XbaI fragment containing the chitinase gene was also ligated into HindIII/XbaI-digested pHDEF1 to create plasmid pHDEF1/CTN.1. Plasmid pHDEF1 is the same as pDEF1 except for two differences: (1) in pHDEF1, a 2 kb EheI/SalI fragment derived from pCEP4 (Invitrogen, Carlsbad, Calif.) containing a hygromycin resistance gene replaced the 19 bp PmeI/SalI fragment of pDEF1; (2) in pHDEF1, expression of the dihydrofolate reductase (DHFR) gene is controlled by a shortened SV40 promoter contained in a 120 bp NheI/Asp718 fragment that replaced the corresponding 212 bp NheI/Asp718 fragment of pDEF1. This 120 bp NheI/Asp718 fragment was prepared by first amplifying a 171 bp PCR fragment with oligonucleotide primer 94–26 (5'-TGATACGGTACCGCCCCATGGCTGACTA-3', SEQ ID NO: 16) (which contains a new Asp718 site), and primer 94–27 (5'-GCAAGTTTGGCGCGAAATCG-3', SEQ ID NO: 17), using as a template the DNA from pDC1 (described in Example 4 of U.S. application Ser. No. 08/847, 218 filed May 1, 1997) that carries the SV40-DHFR cassette, and then digesting this 171 bp PCR fragment with NheI and Asp718.

The DHFR-negative Chinese hamster ovary (CHO) cell line DG44 was transfected with plasmid pDEF1/CTN.1 as described in Example 5 of U.S. application Ser. No. 08/847, 218 filed May 1, 1997. The CHO cell line DG44 was also transfected with plasmid pHDEF1/CTN.1, followed by selection using the following modified procedure. The cells were first selected for hygromycin resistance only, in media (DMEM/F-12 supplemented with 2–10% dialyzed FBS) containing 800 mg/liter of hygromycin (Calbiochem, San Diego, Calif.) and also containing hypoxanthine and thymidine (which therefore made the media non-selective for the DHFR gene). After selecting transfectants that were resistant to hygromycin, the cells were further selected for expression of the DHFR gene by growing them in media lacking hypoxanthine and thymidine. Next, the DHFR-positive and hygromycin-resistant CHO cells were selected in media containing first 10 nM, then 2 nM, and finally 50 nM methotrexate, which resulted in selection of cells expressing higher levels of chitinase.

The supernatant from the pHDEF1/CTN.1 transfected CHO cells containing overexpressed recombinant human chitinase (rH-Chitinase) was purified as follows. In preparation for anion exchange chromatography, the supernatant was diluted 1:3 with 20 mM Tris, pH 7.0 (Buffer A). An anion exchange column, packed with Q-Sepharose Fast Flow Resin (Pharmacia Biotech Inc., Piscataway, N.J.), was equilibrated with Buffer A and loaded with 15L diluted supernatant per 1L resin. The rH-Chitinase was collected in the Flow Through from the Q-Sepharose column and adjusted to 5% Polyethylene Glycol (PEG) 400 (Malinckrodt Baker, Inc., Phillipsburg, N.J.), 30 mM sodium acetate, pH 4.3 in preparation for cation exchange chromatography. A cation exchange column, packed with CM-Sepharose Fast Flow Resin (Pharmacia Biotech Inc., Piscataway, N.J.), was equilibrated with 30 mM sodium acetate, 5% PEG 400, pH 4.3 (Buffer B). The rH-Chitinase sample was loaded onto the CM-Sepharose column at 1 mg per mL resin, and rH-Chitinase was eluted from the column with 40 mM Tris, 5% PEG 400, pH 7.5 (Buffer C). The rH-Chitinase sample was then prepared for hydrophobic interaction chromatography by adding $(NH_4)_2SO_4$ to 1.5 M. A column packed with Macro-Prep Methyl H1C Support, (Bio-Rad Laboratories, Hercules, Calif.,) was equilibrated with 20 mM Tris, 5% PEG 400, pH 7.0 (Buffer D) containing 1.5 M $(NH_4)_2SO_4$. The rH-Chitinase sample was loaded onto the Macro-Prep Methyl column at 1 mg per mL resin. The column was washed with Buffer D containing 1.1 M $(NH_4)_2SO_4$, and rH-Chitinase was eluted with Buffer D containing 0.2 M $(NH_4)_2SO_4$. The purified eluate was exchanged into 150 mM NaCl, 20 mM Tris, pH 7.0 (Buffer E) by membrane filtration.

EXAMPLE 6

Production of Human Chitinase Analogs and Fragments

Recombinant techniques such as those described in the preceding examples may be used to prepare human chitinase polypeptide analogs or fragments. More particularly, polynucleotides encoding human chitinase are modified to encode polypeptide analogs of interest using well-known techniques, e.g., site-directed mutagenesis and polymerase chain reaction. C-terminal and N-terminal deletions are also prepared by, e.g., deleting the appropriate portion of the polynucleotide coding sequence. See generally Sambrook et al., supra, Chapter 15. The modified polynucleotides are expressed recombinantly, and the recombinant polypeptide analogs or fragments are purified as described in the preceding examples.

Residues critical for human chitinase activity are identified, e.g., by homology to other chitinases and by substituting alanines for the native human chitinase amino acid residues. Cysteines are often critical for the functional integrity of proteins because of their capacity to form disulfide bonds and restrict secondary structure. To determine whether any of the cysteines in human chitinase are critical for enzymatic activity, each cysteine is mutated individually to a serine.

A 39 kDa C-terminally truncated fragment of the mature human chitinase protein was prepared as described above in Examples 3 and 5 by introduction of a stop codon after the codon for amino acid 373. This 39 kDa fragment lacked seventy-two C-terminal amino acid residues of the mature protein, including six cysteines, yet retained similar specific enzymatic activity compared to the full length recombinant human chitinase. This result indicates that the missing seventy-two C-terminal residues, including the six cysteines, are not required for enzymatic activity.

Further C-terminal deletions may be prepared, e.g., by digesting the 3' end of the truncated human chitinase coding sequence described in Example 3 with exonuclease III for various amounts of time and then ligating the shortened coding sequence to plasmid DNA encoding stop codons in all three reading frames. N-terminal deletions are prepared in a similar manner by digesting the 5' end of the coding sequence and then ligating the digested fragments into a plasmid containing a promoter sequence and an initiating methionine immediately upstream of the promoter site. These N-terminal deletion analogs or fragments may also be expressed as fusion proteins.

Alternatively, human chitinase polypeptide analogs may also be prepared by full or partial chemical peptide synthesis using techniques known in the art. [See, e.g., synthesis of IL-8 in Clark-Lewis et al., *J. Biol Chem.*, 266:23128–34 (1991); synthesis of IL-3 in Clarke-Lewis et al., *Science*, 231:134–139 (1986); and synthesis by ligation in Dawson et al., *Science*, 266:776–779 (1994).] Such synthetic methods also allow the selective introduction of novel, unnatural amino acids and other chemical modifications.

The biological activities, including enzymatic, antifungal, and extracellular matrix remodeling activities, of the human chitinase polypeptide analogs are assayed by art-recognized techniques, such as those described in Examples 9 to 15 below.

EXAMPLE 7

Production of Human Chitinase Chitin-binding Fragments and Analogs Thereof

A. Generation of SEAP Fusion Proteins

The location of the chitin-binding domain of human chitinase was determined by generating fusion proteins comprising N-terminally truncated portions of human chitinase and testing these products for chitin-binding activity. First, a chimeric protein comprising full length secreted alkaline phosphatase (SEAP) protein (at the N-terminus of the chimeric protein) [Berger et al., *Gene*, 66:1–10 (1988)] fused to the C-terminal 99 amino acids of human chitinase (at the C-terminus of the chimeric protein) was generated as follows. The SEAP component acts as a traceable marker of the chimeric protein.

The SEAP DNA was amplified from the pSEAP2-Control plasmid (Clontech, Palo Alto, Calif.) via polymerase chain reaction (PCR) with primers SEAP Start (SEQ ID NO: 18) and SEAP Stop (SEQ ID NO: 19) that introduced a HindIII site to the 5' end and a multiple cloning region to the 3' end. PCR was carried out using 100 ng of template DNA, 1 μg of each primer, 0.125 mM of each dNTP, 10 mM Tris-HCl, pH 8.4, 50 mM $MgCl_2$ and 2.5 units of Taq polymerase, with an initial denaturation step of 94° C. for four minutes followed by 30 cycles of amplication: 1 minute at 94° C., 1 minute at 60° C., and 2 minutes at 72° C. This PCR-generated cDNA was cloned into the HindIII and ApaI sites of pcDNA3 (Invitrogen, San Diego, Calif.) to generate a vector called pcDNA-SEAP. DNA encoding the C-terminal 99 amino acids of human chitinase (residues 347–445) was also generated by PCR under the same conditions using the primers indicated in Table 1 below, which introduced EcoRI and XbaI sites to the 5' and 3' ends. This PCR-generated chitinase DNA sequence was cloned into the EcoRI and AbaI sites of the multiple cloning region of pcDNA-SEAP.

The resulting construct encoding the chimera was transiently transfected into COS 7 cells by incubation in Dulbecco's modified Eagle medium (DMEM) containing 0.5 mg/ml DEAE dextran, 0.1 mM chloroquine and 10 μg of plasmid DNA for 1.5 hours. The cells then were treated with 10% DMSO in phosphate buffered saline for 45 seconds, washed with serum-free medium and incubated in DMEM supplemented with 1 mM L-glutamine, 100 U/ml penicillin, 100 μg/ml streptomycin and 10% fetal calf serum. After four days, the culture medium was assayed for SEAP activity as described by Flanagan and Leder, *Cell*, 63:185–194 (1990). SEAP activity was readily detectable. Incubation of the culture medium containing this fusion protein with insoluble chitin (Sigma, St. Louis, Mo.) for 1 hour at 4° C. resulted in precipitation of more than 80% of the SEAP activity with the chitin. This result demonstrated that the entire chitin-binding domain is contained within the C-terminal 99 amino acids of human chitinase.

DNA encoding additional chitin-binding domain truncates were generated by PCR and expressed as fusions with SEAP protein as described above. These fusion proteins were assayed for chitin binding activity, with results as displayed in Table 1 below.

TABLE 1

| Truncates tested | Primers used to generate truncates | Chitin-binding Activity |
|---|---|---|
| Amino acids 347–445 | SEAP CBD 1149 (SEQ ID NO: 20) and Hu Chit Stop (SEQ ID NO: 26) | ⊕ |
| Amino acids 374–445 | SEAP CBD 1231 (SEQ ID NO: 21) and Hu Chit Stop (SEQ ID NO: 26) | ⊕ |
| Amino acids 392–445 | SEAP CBD 1285 (SEQ ID NO: 22) and Hu Chit Stop (SEQ ID NO: 26) | ⊕ |
| Amino acids 400–445 | SEAP CBD 1309B (SEQ ID NO: 23) and Hu Chit Stop (SEQ ID NO: 26) | ⊖ |
| Amino acids 409–445 | SEAP CBD 1338 (SEQ ID NO: 24) and Hu Chit Stop (SEQ ID NO: 26) | ⊖ |
| Amino acids 347–431 | SEAP CBD 1149 (SEQ ID NO: 20) and SEAP CBD 1357 (SEQ ID NO: 25) | ⊖ |
| Amino acids 374–431 | SEAP CBD 1231 (SEQ ID NO: 21) and SEAP CBD 1357 (SEQ ID NO: 25) | ⊖ |

TABLE 1-continued

| Truncates tested | Primers used to generate truncates | Chitin-binding Activity |
|---|---|---|
| Amino acids 392–431 | SEAP CBD 1285 (SEQ ID NO: 22) and SEAP CBD 1357 (SEQ ID NO: 25) | ⊖ |
| Amino acids 395–445 | SEAP CBD 1296 (SEQ ID NO: 35) and Hu Chit Stop (SEQ ID NO: 26) | ⊕ |
| Amino acids 397–445 | SEAP CBD 1300 (SEQ ID NO: 36) and Hu Chit Stop (SEQ ID NO: 26) | ⊕ |
| Amino acids 392–443 | SEAP CBD 1285 (SEQ ID NO: 22) and Hu Chit Stop 7 (SEQ ID NO: 37) | ⊖ |

B. Generation of Cysteine Mutation Analogs

To determine whether any of the six cysteines within the 99 C-terminal amino acids of human chitinase were critical for binding chitin, analogs of chitinase fragments were prepared in which each cysteine was mutated individually to a serine. Six PCR products in which each of the six cysteines was individually mutated to serine were generated using the primers indicated in Table 2 below and fused to SEAP cDNA as described above. Chimeric proteins produced by transiently transfected COS cells were assayed for chitin-binding activity as described above. The results of these experiments demonstrated that each of the six cysteines is required for chitin-binding activity.

TABLE 2

| Chitinase binding domain analog tested | Primers used to generate analog | Chitin-binding activity |
|---|---|---|
| C399S | SEAP CBD dC1 (SEQ ID NO: 27) and Hu Chit Stop (SEQ ID NO: 26) | ⊖ |
| C419S | SEAP CBD dC2 (SEQ ID NO: 28) and Hu Chit Stop (SEQ ID NO: 26) | ⊖ |
| C429S | SEAP CBD 1285 (SEQ ID NO: 22) and SEAP CBD dC3 (SEQ ID NO: 29) | ⊖ |
| C439S | SEAP CBD 1285 (SEQ ID NO: 22) and SEAP CBD dC4 (SEQ ID NO: 30) | ⊖ |
| C441S | SEAP CBD 1285 (SEQ ID NO: 22) and SEAP CBD dC5 (SEQ ID NO: 31) | ⊖ |
| C442S | SEAP CBD 1285 (SEQ ID NO: 22) and SEAP CBD dC6 (SEQ ID NO: 32) | ⊖ |

Additional chitin-binding fragments and fragment analogs thereof can be prepared by recombinant techniques or by full or partial chemical synthesis as described in Example 6.

C. Expression of a Chitin-binding Fragment in Yeast

A chitin-binding domain fragment consisting of residues 392–445 of SEQ ID NO: 2 was expressed at high levels in the yeast *Saccharomyces cerevisiae*. An expression construct, α-FLAG-CBD, was designed in which the nucleotides corresponding residues 392–445 of SEQ ID NO: 2 were fused to the 3' terminus of sequence encoding the *S. cerevisiae* α-factor pre-pro sequence [Brake et al., *Proc. Natl. Acad. Sci.* 81:4642–4646 (1984)] and the FLAG epitope tag (Eastman Kodak). To accomplish this, PCR using primers CBDαFLAG (sense; SEQ ID NO: 33) and Hu Chit Stop 5 (antisense; SEQ ID NO: 34) was conducted using full-length human chitinase DNA as a template. The CBDαFLAG primer sequence contains an Asp 718 restriction endonuclease site upstream of a FLAG tag-encoding region that is in-frame with the sequence that encodes the first eight amino acids of the chitin-binding domain fragment 392–445. The Hu Chit Stop 5 primer sequence encodes the C-terminal seven amino acids of the chitin-binding domain fragment followed by Gly-Ala-Gly linked to six histidine residues ($His_6$) which precede a three amino acid segment prior to the translation termination codon. The $His_6$ tract is included to facilitate purification of the expressed product by metal affinity chromatography [as described in Nilsson et al., *Prot. Expr. Punification* 11:1–16 (1997)]. A Not I restriction endonuclease site was included immediately 3' of the stop codon.

The PCR product generated with these primers was digested with Asp 718 and Not I and cloned into the corresponding sites within the expression cassette of plasmid pAYE/VEC, which is derived by modifying pAYE674 [Delta Biotechnology Limited; Sleep et al., *Bio/technology* 9:183–187 (1991)] to add restriction sites to facilitate the incorporation of expression cassettes into pSAC/VEC (described below). The expression cassette within the resulting construct, designated pAYE/AF/CBD, consisted of an in-frame fusion of the nucleotides encoding the *S. cerevisiae* α-factor pre-prosequence and the chitin-binding domain fragment. Upon synthesis, the fusion protein is targeted to the membrane where the mature FLAG-chitin-binding domain fragment-$His_6$ peptide is released from the α-factor pre-pro sequence by the action of the KEX2 protease. Transcription of the α-factor pre-pro-CBD fusion is under the control of the strong promoter PRB1 and the transcription termination sequence from ADH1.

The expression cassette was excised from pAYE/AF/CBD by digestion with Sfi I and Pac I and cloned into the corresponding sites of pSAC/VEC, which is derived by modifying the disintegration vector pSAC35 (Delta Biotechnology Limited; Sleep et al., supra) to incorporate a multiple cloning site. This shuttle vector pSAC35 comprises a complete 2 micron plasmid with a LEU2d selectable marker and two repeated sequences flanking the pUC-derived *E. coli* origin of replication and β-lactamase resistance marker. The resulting pSAC2/AF/CBD plasmid was transformed generally according to Ito et al., *J. Bacteriol.* 153:163–168 (1983), into the *S. cerevisiae* host strain IE41 (a cir° leu2 pep4::URA3 L261; Sleep et al. supra) and selected by growth on leucine deficient media. Following the introduction of pSAC2/AF/CBD into the host strain the repeated sequences undergo a single crossover recombination event, eliminating the pUC sequence. This vector is autonomously replicated, highly stable and has been shown to secrete high levels of product when its host is grown in either selective or non-selective media (Sleep et al., supra).

Following clonal selection, four of the yeast clones were grown for 16 hrs in 2 ml of selective medium at 30° C. The cultures were subsequently transferred to 18 ml of YEPD medium and grown an additional 48 hrs at 30° C. The culture media were harvested and evaluated by SDS-PAGE for the presence of expressed recombinant protein. The gel showed that recombinant chitin-binding domain fragment 392–445 was secreted from all four clones but not from the empty vector control. The secreted protein was positively identified as a chitin-binding domain fragment by its reactivity with a chitin-binding domain-specific monoclonal antibody, 243Q, produced as described in Example 8, on a Western blot.

The secreted chitin-binding domain fragment is highly enriched in the yeast media but is not pure. A preliminary, small-scale metal affinity purification procedure was conducted to obtain pure material. Two ml of Chelating Sepharose Fast Flow (Pharmacia) was deposited into a 12 ml drip column (BioRad). Ten ml of 50 mM $NiSO_4$ was applied to the chelating sepharose to charge it with nickel. Following a 10 ml wash with distilled water, the charged column was equilibrated with 10 ml of Buffer A (20 mM Tris, pH 8, 0.5 M NaCl). Prior to loading, the pH of the culture medium from clone 34A was adjusted to 8 by addition of Tris pH 8 to a final concentration of 20 mM. Fourteen ml of the medium was passed through the column, followed by a 10 ml wash with Buffer A. Recombinant protein was subsequently eluted by sequential applications of Buffer A contaning 10 (2 ml), 50 (2 ml), or 100 mM (3 ml) imidazole. Ten µl of each fraction of the purification procedure was analyzed by SDS-PAGE. The gel showed that 100 mM imidazole eluted essentially pure recombinant chitin-binding domain fragment 392–445. Fractions 2 and 3 of the 100 mM imidazole elution were pooled; the pool was found to contain approximately 0.4 mg/ml of purified protein.

To assess functionality of the recombinant protein, 1 mg of powdered chitin was incubated with 25 µl of the purified chitin-binding domain fragment 392–445 for 1 hour at 4° C. Following the incubation, the insoluble chitin was removed by centrifugation and the amount of protein remaining in the supernatant was compared with that of a chitin-free control medium by SDS-PAGE. An approximately 50% reduction of recombinant protein was observed in the medium treated with chitin. This demonstrates that a least a significant fraction of the recombinant protein retains its capacity to bind chitin.

A second yeast expression construct was designed to express a chitin-binding domain fragment consisting of residues 392–445 of SEQ ID NO: 2 without the FLAG epitope and His6 tags. The construct was assembled as described above except that the PCR primers used to amplify the chitin-binding domain-encoding region were CBDA (sense; SEQ ID NO: 38) and Hu Chit Stop 4 (antisense; SEQ ID NO: 39). Cells were transformed and selected as described above.

A transformed yeast clone expressing recombinant chitin-binding domain was grown overnight at 30° C. in 10 ml of SC-leu-ura medium (Bio101, Vista, Calif.) containing 2% glucose. One ml of this culture was seeded into 100 ml of the same medium and incubated at 30° C. with shaking. After 19 hours, 65 ml of the culture was seeded into 1.2 L of YB2V medium [0.2% glucose, 0.008% $FeCl_3$, 1 g/L $Na_3$ citrate, 25 g/L casamino acids, 13.5 g/L $KH_2PO_4$, 3.8 g/L $(NH_4)_2SO_4$, 4 mM $MgSO_4$, 0.0004% thiamine, trace metals and vitamins] in a 3L fermentor. The fermentation was carried out at 3° C., pH 5.5, with 1200 rpm agitation and an airflow rate of 3 L/min. The pH was controlled using phosphoric acid and ammonium hydroxide. The fermentor was operated under batch conditions for the first 13 hours, after which time feed addition was initiated. Feed medium YF6V.1 [50% glucose, 0.02% $FeCl_3$, 1 g/L $Na_3$ citrate, 50 g/L casamino acids, 2.9 g/L $KH_2PO_4$, 5 g/L $(NH_4)_2SO_4$, 15.2 mM $MgSO_4$, 0.001% thiamine, trace metals and vitamins] was added to the fermentor at a constant rate of 3.6 ml/hour for 4 hours, then the feed rate was increased exponentially with a 5 hour doubling time to a maximum of 9.38 ml/hour. After a total fermentation time of 93 hours, cells were harvested by centrifugation. 1.6 L of the broth was centrifuged for 40 minutes at 4° C., 5000×g. The cell pellet was discarded and the supernatant was filtered through a pre-filter and a 0.2 µM filter.

Purification of the recombinant chitin-binding domain was accomplished by passing culture medium from the fermentation through a chitin bead column. A 25 ml bed volume of chitin beads (New England Biolabs) was prepared in a 50 ml column (Amicon), prewashed with 250 ml of 1% SDS, and equilibrated with 250 ml Buffer A (20 mM Tris, pH 8, 500 mM NaCl) at a flow rate of 2 ml/min. Clarified medium was passed through the chitin bead column at a rate of 1 ml/min. Following a 250 ml wash with Buffer A, protein was eluted from the beads with 50% acetonitrile, 0.1% trifluoroactetate and collected into 4 ml fractions. Acetonitrile was evaporated from the eluate by vacuum centrifugation. Analysis of elution fractions by SDS-polyacrylamide gel electrophoresis and protein quantitation revealed that 94% of the purified chitin-binding domain was recovered in 3 consecutive fractions. In total, 109 mg of chitin-binding domain was obtained from 130 ml of fermentation medium. Analysis of the purified protein by MALDI mass spectrometry (Perseptive Biosystems) shows a single peak with molecular weight of 5911.9, a value that corresponds favorably to the predicted mass of 5909.8. In a test of its functional integrity, 20 µg of the purified chitin-binding domain mixed with 250 µl of chitin beads resulted in >95% of the peptide being bound to the beads.

EXAMPLE 8

Preparation of Monoclonal Antibodies to Human Chitinase

The following two protocols (multiple challenge or single shot immunizations) may be used to generate monoclonal antibodies to human chitinase. In the first protocol, a mouse is immunized by periodic injection with recombinant human chitinase (e.g., 10–20 µg emulsified in Freund's Complete Adjuvant) obtained as described in any of Examples 3 through 6. The mouse is given a fmal pre-fusion boost of human chitinase in PBS, and four days later the mouse is sacrificed and its spleen removed. The spleen is placed in 10 ml serum-free RPMI 1640, and a single cell suspension is formed by grinding the spleen between the frosted ends of two glass microscope slides submerged in serum-free RPMI 1640, supplemented with 2 mM L-glutamine, 1 mM sodium pyruvate, 100 units/ml penicillin, and 100 µg/ml streptomycin (RPMI) (Gibco, Canada). The cell suspension is filtered through sterile 70-mesh Nitex cell strainer (Becton Dickinson, Parsippany, N.J.), and is washed twice by centrifuging at 200 g for 5 minutes and resuspending the pellet in 20 ml serum-free RPMI. Splenocytes taken from three naive Balb/c mice are prepared in a similar manner and used as a control. NS-1 myeloma cells, kept in log phase in RPMI with 11% fetal bovine serum (FBS) (Hyclone Laboratories, Inc., Logan, Utah) for three days prior to fusion, are centrifuged at 200 g for 5 minutes, and the pellet is washed twice as described in the foregoing paragraph.

One$\times 10^8$ spleen cells are combined with $2.0 \times 10^7$ NS-1 cells and centrifuged, and the supernatant is aspirated. The cell pellet is dislodged by tapping the tube, and 1 ml of 37° C. PEG 1500 (50% in 75 mM Hepes, pH 8.0) (Boehringer Mannheim) is added with stirring over the course of 1 minute, followed by the addition of 7 ml of serum-free RPMI over 7 minutes. An additional 8 ml RPMI is added and the cells are centrifuged at 200 g for 10 minutes. After discarding the supernatant, the pellet is resuspended in 200 ml RPMI containing 15% PBS, 100 µM sodium hypoxanthine, 0.4 µM aminopterin, 16 µM thymidine (HAT) (Gibco), 25 units/ml IL-6 (Boehringer Mannheim) and 1.5× $10^6$ splenocytes/ml and plated into $10^o$ Corning flat-bottom 96-well tissue culture plates (Corning, Corning N.Y.).

On days 2, 4, and 6, after the fusion, 100 µl of medium is removed from the wells of the fusion plates and replaced with fresh medium. On day 8, the fusion is screened by ELISA, testing for the presence of mouse IgG binding to human chitinase as follows. Immulon 4 plates (Dynatech, Cambridge, Mass.) are coated for 2 hours at 37° C. with 100 ng/well of human chitinase diluted in 25 mM Tris, pH 7.5. The coating solution is aspirated and 200 ul/well of blocking solution [0.5% fish skin gelatin (Sigma) diluted in CMF-PBS] is added and incubated for 30 min. at 37° C. Plates are washed three times with PBS with 0.05% Tween 20 (PBST) and 50 μl culture supernatant is added. After incubation at 37° C. for 30 minutes, and washing as above, 50 μl of horseradish peroxidase conjugated goat anti-mouse IgG(fc) (Jackson ImmunoResearch, West Grove, Pa.) diluted 1:3500 in PBST is added. Plates are incubated as above, washed four times with PBST, and 100 μL substrate, consisting of 1 mg/ml o-phenylene diamine (Sigma) and 0.1 μl/ml 30% $H_2O_2$ in 100 mM citrate, pH 4.5, are added. The color reaction is stopped after 5 minutes with the addition of 50 μl of 15% $H_2SO_4$. $A_{490}$ is read on a plate reader (Dynatech). Selected fusion wells are cloned twice by dilution into 96-well plates and visual scoring of the number of colonies/well after 5 days. The monoclonal antibodies produced by hybridomas are isotyped using the Isostrip system (Boehringer Mannheim, Indianapolis, Ind.).

Alternatively, a second protocol utilizing a single-shot intrasplenic immunization may be conducted generally according to Spitz, Methods Enzymol., 121:33–41 (1986). The spleen of the animal is exposed and recombinant human chitinase (e.g., 10–20 μg in PBS at a concentration of about 0.02% to 0.04%, with or without an aluminum adjuvant), obtained as described in any of Examples 3 through 6, is injected, after which the spleen is returned to the peritoneal cavity and the animal is stitched closed. Three days later, the mouse is sacrificed and its spleen removed. A spleen cell suspension is prepared, washed twice with RPMI 1640 supplemented with 3% fetal calf serum (FCS), and resuspended in 25 ml of the same medium. Myeloma cells (NS-O) are collected at logarithmic growth phase, washed once and added to the spleen cell suspension in a 50 ml tube, at a ratio of 3:1 or 2:1 (spleen cells:myeloma cells). The mixture is pelleted at about 450×g (1500 rpm), the supernatant aspirated, and the pellet loosened by tapping the tube. Fusion is performed at room temperature by adding 1 ml of polyethylene glycol (PEG) 1500 over 1 minute, with constant stirring. The mixture is incubated for another minute, then 1 ml of warm RPMI (30 to 37° C.) is added over 1 minute followed by 5 ml RPMI over 3 minutes and another 10 ml RPMI over another 3 minutes. The cell suspension is centrifuged and resuspended in about 200 ml of HAT selective medium consisting of RPMI 1640 supplemented with 100 U/ml penicillin, 100 μg/ml streptomycin, 20% FCS, 100 μM hypoxanthine, 0.4 μM aminopterin and 16 μM thymidine. The cell suspension is dispensed in 1 ml volumes into tissue culture plates and incubated at 37° C. in a humid atmosphere with 5% $CO_2$-95% air for 8 to 10 days. Supernatants are aspirated and the cells are fed with 1 ml HAT medium per well, every 2 to 3 days according to cell growth. Supernatants of confluent wells are screened for specific antibodies and positive wells are cloned.

Using the above protocols, several monoclonal antibodies with reactivity to human chitinase were generated. For fusion 243, each of five 6–12 week old Balb/c mice was prebled on day 0 and then immunized by subcutaneous injection with 10–20 μg recombinant human chitinase prepared as described in Example 5, emulsified in complete Freunds adjuvant. On days 21, 42 and 60 each mouse was boosted with 50 μg of the same recombinant human chitinase in incomplete Freunds adjuvant. Mouse #2483 was additionally given 20 μg of recombinant human chitinase daily on days 216 through 219. On day 220 the spleen of mouse #2483 was removed sterilely and treated as described above. Briefly, a single-cell suspension was formed by grinding the spleen between the frosted ends of two glass microscope slides submerged in serum free RPMI 1640, supplemented with 2 mM L-glutamine, 1 mM sodium pyruvate, 100 units/ml penicillin, and 100 μg/ml streptomycin (RPMI) (Gibco, Canada). The cell suspension was filtered through a sterile cell strainer (Becton Dickinson, Parsippany, N.J.), and washed twice with serum free RPMI by centrifuging at 200×g for 5 minutes and resuspending the pellet in 20 ml serum free RPMI. Thymocytes taken from naive Balb/c mice were prepared in a similar manner.

NS-1 myeloma cells, kept in log phase in RPMI with 10% Fetal Clone serum (FCS) (Hyclone Laboratories, Logan, Utah) for three days prior to fusion, were centrifuged at 200×g for 5 minutes, and the pellet was washed twice and resuspended in 10 ml serum free RPMI as described above.

Spleen cells were combined with NS-1 cells at a ratio of 5:1, centrifuged at 200×g and the supernatant was aspirated. The cell pellet was dislodged by tapping the tube and 2 ml of 37° C. PEG 1500 (50% in 75 mM Hepes, pH 8.0) (Boehringer Mannheim) was added with stirring over the course of 1 minute, followed by adding 14 ml of serum free RPMI over 7 minutes. An additional 16 ml RPMI was added and the cells were centrifuged at 200×g for 10 minutes. After discarding the supernatant, the pellet was resuspended in 200 ml RPMI containing 15% FBS, 100 μM sodium hypoxanthine, 0.4 μM aminopterin, 16 μM thymidine (HAT; Gibco), 25 units/ml recombinant human IL-6 (Boehringer Mannheim) and 1.5×10⁶ thymocytes/ml. The suspension was dispensed into ten 96-well flat bottom tissue culture plates (Corning, United Kingdom) at 200 μl/well. Cells in plates were fed 3 to 5 times before screening by aspirating approximately 100 μl from each well with a 20-gauge needle (Becton Dickinson), and adding 100 μl/well of the plating medium described above except containing 10 units/ml IL-6 and lacking thymocytes.

Supernatants from fusion 243 were screened initially by ELISA on the immunogen (full length human chitinase), and detected with goat anti-mouse IgG (fc) horseradish peroxidase conjugate. To ensure clonality, positive wells chosen from each fusion were subdloned 4 times by limiting dilution, using media lacking aminopterin. Cloning was completed for cell lines 243K, 243M and 243Q.

Isotypes were determined for the monoclonal antibodies from the two cell lines using either the Isostrip kit (Boehringer Mannheim) or an ELISA using isotype specific reagents (Zymed Laboratories, South San Francisco, Calif.). All antibodies are IgG1 isotype.

To test whether any of these bear specificity toward the chitin-binding domain, each antibody was used to probe a western blot containing the full length chitinase, the C-terminally truncated chitinase (amino acids 1–373), and the recombinant chitin-binding domain (amino acids 392–445) produced in yeast. Three antibodies, 243K, 243M, and 243Q, bound to the full-length chitinase and to the chitin-binding domain but not to the C-terminal truncate.

All combinations of all three antibodies were tested for applicability to use in a sandwich ELISA format. Nunc-Immuno Module plates were coated with 125 μl of first antibody at 2 μg/ml and incubated overnight at 4° C. The antibody solution was then replaced with 300 μl/well of blocking solution (5% Teleostean gelatin, 0.05% Proclin 300 in CMF-PBS). After a 30 min incubation at room temperature, the blocking solution was replaced with 20 ng/ml recombinant chitin-binding domain in Omni Diluent (1% Teleostean gelatin, 0.05% Tween 20, 0.05% Proclin in CMF-PBS) and incubated 30 min at 37° C. Wells were washed 5 times with wash buffer (145 mM NaCl, 1.5%

Tween 20) then received 0.25 µg/ml of biotinylated second antibody. After a 30 min incubation at 37° C., wells were again washed 5 times, treated with 100 µl of streptavidin-conjugated horseradish peroxidase (Pierce), and incubated 30 min at 37° C. Following another 5 washes, wells received 100 µl of substrate (0.01 g/ml tetramethylbenzidine in dimethyl sulfoxide diluted 1:100 into 100 mM sodium acetate trihydrate, pH 5.5, 0.015% $H_2O_2$) and were incubated at room temperature in the dark. After 30 min, 100 µl of 1N $H_2SO_4$ was added to stop the reaction and absorbance at wavelengths of 450 and 630 nm was determined. This approach identified 243Q (first antibody) and 243M (second antibody) as the combination which delivered the greatest signal relative to all other combinations. The hybridoma 243Q producing antibody 243Q was deposited on Mar. 25, 1999 with American Type Culture Collection, 10801 University Blvd., Manassas, Va. 20110-2209 and was assigned Accession No. HB-12688. The hybridoma 243M producing antibody 243M was deposited on Mar. 25, 1999 with American Type Culture Collection, 10801 University Blvd., Manassas, Va. 20110-2209 and was assigned Accession No. HB-12687.

EXAMPLE 9

Catalytic Activity of Recombinant Chitinase

Chitotriosidase (chitinase) activity was measured using the fluorogenic substrate 4-methylumbelliferyl-β-D-N,N', N"-triacetylchitotriose (4 MU-chitotrioside, Sigma Chemical, St. Louis, Mo.) in McIlvain buffer (Hollak et al., supra). Ten µl samples of the recombinant product described in Example 5A were combined with 10 µl bovine serum albumin (10 mg/ml), 15 µl fluorogenic substrate (2.71 mM), and 65 µl buffer (0.1M citric acid, 0.2M sodium phosphate, pH 5.2) in a total volume of 100 µl. Reactions were incubated at 37° C. for 15 minutes, then the reaction was stopped with the addition of 2 ml of 0.3M glycine/NaOH buffer (pH 10.6). The fluorescent cleavage product, 4-methylumbelliferone, was monitored with a fluorimeter (SLM-AMINCO Instruments, Inc., Rochester, N.Y.) at 450 nm. To obtain a standard curve, several substrate concentrations were combined with excess bacterial chitinase to ensure that substrate was completely cleaved. The known quantity of 4-MU was then correlated to the fluorescence signal from the fluorimeter and linear regression was used to determine a standard curve. The signal produced with diluted purified recombinant chitinase in the assay was then used to interpolate the nmol quantity of substrate cleaved by the enzyme during the reaction time. This number was then divided by the concentration of protein to obtain the nmol/min per mg protein (determined by $A_{280}$ and calculated molar extinction coefficient).

The chitotriosidase activity of the recombinant human chitinase produced in COS cells as described in Example 5A was determined to be 90 nmol/min per mg protein. Any of the human chitinase fragment products of the present invention can also be tested for chitinase enzymatic activity in this manner.

EXAMPLE 10

Anti-fungal Activity of Chitinase Fragment Products In Vitro

Conventional anti-fungal agents that have been conjugated to human chitinase products of the invention can be tested for inhibition of fungal growth in vitro. The two fungi *Candida albicans* and *Aspergillus fumigatis* are serious pathogens for immunocompromised patients. Both Candida and Aspergillus are grown in RPMI growth media at 37° C. to approximately 10,000–50,000 colony forming units (CFU) per ml. Serial dilutions of the test drug are added to cultures, and fungal growth is assessed at 24 hours by turbidity of cultures.

The anti-fungal activity of the test drug may also be evaluated in an agar diffusion assay, in a broth assay according to National Committee on Clinical Laboratory Standards, and in a cell wall inhibition assay according to Selitrennikoff, *Antimicrob. Agents Chemother.*, 23:757–765 (1983).

In the agar diffusion assay, approximately $1 \times 10^6$ cells/ml of *Candida albicans* (ATCC no. 90028) is inoculated into 1.5% agar (RPMI 1640 media buffered with 2-(N-morpholino)propanesulfonic acid (MOPS), pH 7.0. A disk containing a set amount, e.g., 50 µg of the test drug or a control is placed on the agar, and the zone of growth inhibition is measured.

In the broth assay, a set amount, e.g., 50 µg/ml of the test drug or a control is added with a certain concentration of the test fungal orgamnsm to RPMI 1640 media buffered with MOPS, pH 7.0. The samples are incubated at 35° C., with shaking at 120 rpm, for 48 hours, and then growth is evaluated by measuring the turbidity of the suspension. Appropriate concentrations of test fungal organism include the following: $2.5 \times 10^4$ cells/ml of *Candida albicans* (ATCC no. 90028); $5'10^4$ cells/ml of *Candida albicans*-polyene resistant (ATCC no. 38247); $1 \times 10^4$ cells/ml of *Aspergillus fumigatus* (ATCC no. 16424); $1 \times 10^4$ cells/ml of *Neurospora crassa* (ATCC no. 18889); and $1 \times 10^4$ cells/ml of *Saccharomyces cerevisiae* (ATCC no. 26108).

The os-1 whole cell assay, which identifies inhibitors of fungal cell wall biosynthesis, is conducted essentially according to Selitrennikoff, supra, using an inoculum of $1.5 \times 10^5$ protoplasts/ml embedded in agar (Vogel's Medium N, 7.5% sorbitol, 1.5% sucrose, 10 µg/ml nicotinamide and 1% agar) incubated at 25° C. for 72 hours. The cultures are monitored for changes in growth and morphology after disks containing a set amount, e.g., 50 µg of test drug or control are placed on the agar medium. The os-1 cell is a mutant strain of *Neurospora crassa* that grows as protoplasts without cell walls when incubated under certain conditions at 37° C., but regenerates a cell wall under the appropriate conditions when the temperature is shifted to about 22° C. Samples that inhibit growth are considered fungal growth inhibitors and samples that prevent cell wall regeneration, but do not kill the cells, are considered cell wall-specific inhibitors.

EXAMPLE 11

Anti-fungal Activity of Recombinant Chitinase In Vivo in Mice

The pharmacokinetics of recombinant human chitinase in mice were determined as follows. Female Balb/c mice, 6–8 weeks old, were administered 0.5 mg/kg, 5.0 mg/kg and 50 mg/kg recombinant human chitinase by intravenous injection in the tail vein. For each dose, mice were terminally bled at 0.01, 0.25, 1, 8 and 24 hours after injection (2 animals were used per time point per dosage). Serum samples were then assayed for chitinase activity and concentration. Results are shown in Table 3 below.

TABLE 3

| Dose (mg/kg) | AUC (µg/ml/h) | Vss (ml/kg) | cL (ml/h/kg) | MRT (h) | half-life (h) | Cmax (µg) |
| --- | --- | --- | --- | --- | --- | --- |
| 0.5 | 31.24 | 12.03 | 16.01 | 0.75 | 0.74 | 22.30 |
| 5.0 | 278.50 | 13.61 | 17.95 | 0.76 | 1.38 | 162.84 |
| 50.0 | 2505.83 | 52.92 | 19.95 | 2.65 | 2.33 | 1179.19 |

AUC: area under curve to time infinity
Vss: steady state volume of distribution
cL: clearance
MRT: total body mean residence time
Cmax: peak serum concentration The pharmacokinetics of chitinase fragment products of the invention or therapeutic agents comprising such chitinase fragment products may be assessed in the same manner.

Several animal models have been developed for testing efficacy of anti-fungal compounds [see Louie et al., *Infect. Immun.*, 62: 2761–2772, 1994; Kinsman et al., *Antimicrobial Agents and Chemotherapy*, 37: 1243–1246, 1993; Nakajima et al., *Antimicrobial Agents and Chemotherapy* 39: 1517–1521, 1995; Tonetti et al., *Eur. J. Immunol.*, 25:1559–1565 (1995); Denning and Stevens, *Antimicrob. Agents Chemother.*, 35:1329–1333 (1991); see also Stevens, *J. Mycol. Med.*, 6(suppl.I):7–10 (1996)]. Briefly, the animal host is infected with the fungi, varying doses of test drug are administered to the animals, and their survival is measured over time. Comparative experiments may be performed using a conventional anti-fungal agent alone or the same agent conjugated to a chitinase fragment product, to determine if conjugation of the agent to the chitin-binding fragment products improves its anti-fungal efficacy. Specifically, acute systemic candidiasis is achieved in mice by intraperitoneal or intravenous challenge of $10 \times 10^6$ CFU *Candida albicans*. The therapeutic agents are administered before or at 1 to 5 hours after challenge, and the number of survivors is determined after five days. In addition, the mice can be sacrificed and fungal load can be determined in specific organs such as brain, kidney, lung, liver and spleen. Alternatively, the mice are challenged with lower doses of fungi, e.g., Aspergillus ($8-10 \times 10^6$ CFU) or Candida ($1 \times 10^6$ CFU), in which case survival can be measured at more distant time points, e.g., 45 days. The long term fungicidal/fungistatic activity of a test drug may be evaluated by continuing therapy for a week or more, e.g., 11 days, and following the animals over several weeks, e.g., 18 days to one month. Effective anti-fungal agents enhance the long term survival of animals and reduce fungal load in blood and organs.

EXAMPLE 12

Activity of Chitinase In Vivo in a Rabbit Model of Invasive Aspergillosis

The efficacy of therapeutic agents comprising chitinase fragment products is assessed in an immunosuppressed rabbit model of invasive aspergillosis which has been used for over ten years to evaluate a variety of anti-fungal therapies. See, e.g., Andriole et al., *Clin. Infect. Dis.*, 14(Suppl. 1):S134-S138 (1992). The study is conducted generally according to Patterson et al., *Antimicrob. Agents Chemother.*, 37:2307–2310 (1993) or George et al., *J. Infect. Dis.*, 168:692–698 (1993). Briefly, on day one the rabbits are given cyclophosphamide (200 mg) intravenously to render them leukopenic, followed by triamcinolone acetonide (10 mg) subcutaneously each day for the duration of the experiment. On day two, 24 hours after immunosuppression, the animals are challenged intravenously with about $10^6$ (lethal challenge) or about $10^5$ (sublethal challenge) *A. fumigatus* conidia. Anti-fungal therapy with the test agents is initiated at 24 hours after challenge or 48 hours before challenge (for prophylaxis) and is continued for 5 to 6 days or until death. Exemplary doses of conventional anti-fungal agents are 1.5 or 0.5 mg/kg/day intravenous amphotericin B, 60 or 120 mg/kg/day oral fluconazole and 100 mg/kg/day oral 5-fluorocytosine. Control rabbits are not treated with any anti-fungal agent.

At autopsy or death, semiquantitative fungal cultures and histopathologic examination are conducted on the liver, spleen, kidneys, lungs and brain. Cultures of the heart, urine and blood may also be performed. Blood samples are obtained at intervals and assayed for white blood cell counts and circulating Aspergillus carbohydrate antigen using an ELISA assay. The effect of treatment with the test drug is evaluated on three endpoints: reduction in mortality rate, reduction in number of Aspergillus organisms cultured from target organs (fungal burden), and reduction in level of circulating Aspergillus antigen. Effective anti-fungal agents reduce mortality and/or fungal load.

Alternatively, pulmonary aspergillosis may be evaluated in this model generally according to Chilvers et al., *Mycopathologia*, 108:163–71 (1989), in which the immunosuppressed rabbits are challenged with intratracheal instillation of *Aspergillus fumigatus* conidia, followed by bronchoalveolar lavage on days 1, 2, 4, 7 and 10 following challenge; fungal culture, chitin assay, white cell counts and histopathology are performed on the lavage fluids to determine infective load within the lung. Effective anti-fungal agents reduce the infective load or inflammation within the lung.

EXAMPLE 13

Activity of Chitinase In Vivo in a Rabbit Model of Disseminated Candidiasis

The efficacy of therapeutic agents comprising chitinase fragment products is assessed in a rabbit model of disseminated candidiasis generally according to Rouse et al., *Antimicrob. Agents Chemother.*, 36:56–58 (1992). New Zealand white rabbits are infected systemically with about $3 \times 10^6$ *Candida albicans* blastospores. Anti-fungal therapy with the test drugs is initiated 48 hours after challenge with Candida (or before challenge for prophylaxis) and is continued for, e.g., four days. Surviving animals are sacrificed, and fungal cultures are performed on the aortic valve with attached vegetation, lung, kidney and spleen. Fungal cultures and histopathological examination may also be performed on these and other organs, such as liver, brain, and heart. Urine and blood cultures may also be done. The effect of the anti-fungal therapy on mortality and circulating or tissue fungal burden is determined.

Bayer et al., *Antimicrob. Agents Chemother.*, 19:179–184 (1981), describes a model in which rabbits are inoculated intraperitoneally with about $5 \times 10^8$ CFU Candida albicans. A saline peritoneal aspirate is obtained and cultured from each animal four days after intraperitoneal inoculation, and animals with a positive fungal culture aspirate are randomly assigned to control or treatment groups. Anti-fungal treatment with the test agents is begun seven days after challenge. The eyes of all rabbits are evaluated using indirect ophthalmoscopy, as disseminated candidiasis may result in Candida endophthalmitis. Animals are sacrificed at 7, 11 and 14 days after initiation of therapy and their abdomens inspected for evidence of peritonitis and intraabdominal abscess formation. Eyes are examined for macroscopic lesions. Tissue samples from peritoneal abscesses, all other visible abscesses, kidneys, livers, spleens and ocular structures are weighed, homogenized in brain heart infusion broth, serially diluted and cultured to determine the CFU per gram of tissue. Renal and peritoneal abscesses are also fixed in 10% neutral formaldehyde and examined for histopathology. Sections are stained with periodic acid-Schiff reagent to determine the fungal burden and fungal morphology. Effect of the test drugs on improving survival and reducing fungal burden is evaluated.

EXAMPLE 14

Activity of Chitinase In Vivo in a Rabbit Model of Fungal Endophthalmitis

The efficacy of therapeutic agents comprising chitinase fragment products is assessed in a rabbit model of Candida endophthalmitis, generally according to Park et al., *Antimicrob. Agents Chemother.*, 39:958–963 (1995). Briefly, New Zealand albino rabbits, 2 to 2.5 kg, are infected with an intravitreal inoculation of about 1,000 CFU of Candida albicans. Endophthalmitis is confirmed 5 days after inoculation by indirect ophthalmoscopy, and is defmed as moderate to severe vitreous haze with partial or complete obscuration of greater than 50% of the retinal and choroidal vasculature. The vitreous turbidity is graded on a scale, and the fundus appearance may be graded and documented by fundus photography. The rabbits are then treated with test agents for 2 to 4 weeks. Exemplary doses of conventional anti-fungal agents are 80 mg/kg/day of oral fluconazole and 100 mg/kg every 12 hours of oral 5-fluorocytosine.

The treatment effect is assessed at 2 and 4 weeks after therapy by indirect ophthalmoscopy, quantitative fungal culture, and histopathology. For quantitative fungal culture, the eyes are dissected and weighed, and a weighed fraction of each sample is homogenized and cultured on brucella agar-5% horse blood plates for 48 hours at 35° C. in 5 to 10% $CO_2$. The homogenized sample may also be diluted 10- or 100-fold with sterile saline before plating. The colonies are counted and the total CFU in the eye calculated on the basis of the growth yielded from the measured fractions of sample. Treatment effect is assessed in terms of a reduction in the total intraocular fungal burden. For histopathology, representative eyes are removed, fixed in formnalin, embedded in plastic, and sliced into 5 µm sections. The sections are stained with hematoxylin-eosin or Gomori's methenamine silver stain and examined by light microscopy for inflammation, fibrous organization and fungal elements. The effect of the anti-fungal agents on reducing mortality, reducing fungal load, or reducing the inflammation associated with fungal infection, is evaluated.

Alternatively, a rabbit model of Aspergillus endophthaimitis may be used generally according to Jain et al., *Doc. Ophthalmol.*,69:227–235 (1988). Briefly, New Zealand white rabbits are inoculated in one eye with about forty spores of *Aspergillus fumigatus*. Their contralateral (control) eyes receive a similar but sterile inoculum. After treatment with the test agents, the rabbits' eyes may be evaluated for clinical appearance, electroretinogram waveforms, indirect ophthalmoscopy, quantitative fungal culture, and histopathology. Clinically evident endophthalmitis typically develops within three to seven days after inoculation.

EXAMPLE 15

Activity of Chitinase In Vivo in a Rabbit Model of Fungal Endocarditis

The efficacy of therapeutic agents comprising chitinase fragment products is assessed in a rabbit model of Candida endocarditis generally according to Witt and Bayer, *Aninmicrob. Agents Chemother.*, 35:2481–2485 (1991). See also Longman et al., *Rev. Infect. Dis.*, 12(Suppl. 3):S294–298 (1990). Sterile thrombotic endocarditis is produced in New Zealand white rabbits by transaortic valvular placement of a sterile polyethylene catheter (internal diameter, 0.86 mm), which remained in place for the duration of the study. Infective endocarditis is then established 48 hours after catheterization by intravenous injection of about $2 \times 10^7$ C. albicans blastospores. Alternatively, *C. parapsilosis* may be used. Anti-fungal therapy with test agents is initiated either 24 hours before or 24 to 60 hours after fungal challenge. Therapy is continued daily for 9 or 12 days. Exemplary doses of conventional anti-fungal agents are 1 mg/kg/day intravenous amphotericin B, 50 mg/kg/day or 100 mg/kg/day intravenous or intraperitoneal fluconazole. Control rabbits are given no anti-fungal agent. At sacrifice, hearts are removed and the m position of the indwelling catheter verified. Cardiac vegetations from each animal are removed, pooled, weighed and homogenized in 1 ml of sterile saline. The homogenate is serially diluted and quantitatively cultured on yeast potassium dextrose agar at 35° C. for 48 hours. Culture-negative vegetations are considered to contain less than 2 $\log_{10}$ CFU/gram on the basis of average vegetation weight.

EXAMPLE 16

Chitin-binding and Chitin Hydrolytic Activity of Fragments of Human Chitinase A. The chitin-binding domain is essential for binding of chitinase to chitin The chitin-binding and chitotriosidase activity of full length chitinase (445 amino acids) was compared to the activity of the C-terminally truncated fragment (amino acids 1–373) described in Example 5 above. Full length chitinase and chitinase fragment were prepared as follows. The expression constructs for full-length chitinase (MO-13B) and for the 373 amino acid C-terminally truncated fragment, described above in Example 5, were transfected into COS cells. After 24 hours, culture media [Dulbecco's modified Eagle medium (Gibco)+10% fetal bovine serum+1 mM L-glutamine+100 U/ml penicillin+100 µg/ml streptomycin] were replaced with media lacking fetal bovine serum. Cells were cultured for another 3 days, after which media were harvested and assayed for hydrolytic and chitin-binding activities.

Levels of chitotriosidase activity, determined as described in Example 9, were nearly identical in culture media obtained from cells expressing full-length chitinase (57.6 nmol/ml/min) and culture media from cells expressing the C-terminally truncated fragment (57.8 nmol/ml/min). This is consistent with results reported in Example 6. The substrate used for determining chitotriosidase activity (as in Example 9) is triacetylchitotriose, a soluble, three residue oligosaccharide.

To compare chitin-binding activity, crab shell chitin (Sigma) was ground to a fine powder using a mortar and pestle, washed three times with equilibration buffer (20 mM Tris, pH 8, 500 mM NaCl), and resuspended to 100 mg/ml. One hundred Al of the chitin suspension was added to 1 ml of transfected COS cell medium and the mixture was incubated 4 hr at 4° C. with continuous end-over-end mixing. Following incubation, the chitin was pelleted by centrifugation (5 min, 12,000×g). Equivalent volumes of supernatant were supplemented with Laemmli buffer and 50 mM dithiothreitol (DTT), boiled, and electrophoresed through a 12% polyacrylamide gel (Novex). Subsequent analysis of the gel by Western blotting using a chitinase-specific monoclonal antibody (206A) revealed that no full length chitinase remained in the supernatant, i.e., that all of the full length chitinase had bound to the chitin and had been pelleted with the chitin. In contrast, there was no discernible reduction in the quantity of C-terminally truncated fragment (amino acids 1–373) in the supernatant, indicating that the truncate had not bound to the chitin.

These observations indicate that the C-terminal 72 amino acids of human chitinase are required for chitin-binding activity but not for hydrolysis of triacetylchitotriose.

B. The chitin-binding Domain is Essential for Hydrolysis of Chitin but not Triacetylchitotriose The substrate used in Example 16A above for determining chitotriosidase activity is a soluble, three residue oligosaccharide. Native chitin, however, is a long chain, insoluble polysaccharide. Thus, it is possible that the ability of an enzyme to hydrolyze the small analog may not predict its ability to hydrolyze chitin. To compare the chitinolytic activity of full-length chitinase (445 amino acids) and the C-terminally truncated fragment (amino acids 1–373), crab shell chitin was incorporated into an agarose gel. Wells were cut into the solidified gel and loaded with either the full length chitinase or the truncate. After incubation, zones of clearing around the well indicated the extent of hydrolysis of the chitin.

The experiment was conducted as follows. A suspension of 0.4% chitin and 1.5% agarose was boiled in 20 mM sodium phosphate, pH 6, poured to a thickness of 2 mm in a 10 cm petri dish, and allowed to solidify. Wells 3 mm in diameter were cut into the agarose/chitin matrix. Prior to loading wells, the recombinant proteins in the media from transfected COS cells were concentrated 70-fold over a 30,000 molecular weight cutoff filter device (Millipore). Equivalent quantities of the full-length and C-terminally truncated recombinant proteins were loaded into adjacent wells. A third well was loaded with concentrated media from mock-transfected COS cells. Repeated equivalent loadings of each well were required in order to produce a visible zone of clearing. A zone of clearing that extended 3 mm from the periphery of the well was observed surrounding the well loaded with concentrated medium from COS cells producing full-length chitinase. No clearing was seen around the wells containing either the truncate-containing media or mock transfected cell culture media.

These observations demonstrate that the C-terminal 72 amino acids of human chitinase are required for hydrolysis of chitin.

EXAMPLE 17

Chemical Modification of Recombinant Chitin-binding Domain By Conjugation to Other Agents In order to test whether the chitin-binding domain is amenable to serving as a carrier for small molecule pharmaceuticals, a chitin-binding domain consisting of amino acids 392–445 of human chitinase was chemically conjugated with either biotin or rhodamine, as follows.

Biotinylation was accomplished using the Pierce EZ-link Sulfo-NHS-Biotinylation Kit (Pierce) according to the manufacturer's protocol. The NHS linkage was expected to target free amines which, on the chitin-binding domain, are found at the N-terminus and at lysines 402 and 440. Consistent with these expectations, MALDI mass spectrometry revealed three biotinylated species with masses corresponding to the presence of one, two, or three biotin molecules per peptide. The majority (>60%) was triple biotinylated.

Using a succinimidyl linkage (Molecular Probes), rhodamine was attached to the N-terminus of the chitin-binding domain.

Binding of either the biotin- or rhodamine-labeled peptide to chitin was indistinguishable from the binding properties of the non-labeled peptide. This suggests that the chitin-binding domain is able to tolerate some chemical modification without an impact on its chitin-binding activity.

Numerous modifications and variations of the above-described invention are expected to occur to those of skill in the art. Accordingly, only such limitations as appear in the appended claims should be placed thereon.

---

What is claimed is:

1. A polypeptide selected from the group consisting of polypeptides consisting of the sequence of amino acid residues X through Y of SEQ ID NO: 2, wherein X is a consecutive integer from 392 through 397 and Y is 445.

2. The polypeptide of claim 1 selected from the group consisting of a polypeptide having the sequence of amino acid residues 392 through 445 of SEQ ID NO: 2, a polypeptide having the sequence of amino acid residues 395 through 445 of SEQ ID NO: 2, and a polypeptide having the sequence of amino acid residues 397 through 445 of SEQ ID NO: 2.

3. The polypeptide of claim 2 having the sequence of amino acid residues 392 through 445 of SEQ ID NO: 2.

4. The polypeptide of claim 2 having the sequence of amino acid residues 395 through 445 of SEQ ID NO: 2.

5. The polypeptide of claim 2 having the sequence of amino acid residues 397 through 445 of SEQ ID NO: 2.

6. A fusion protein comprising the polypeptide of claim 1 fused to a heterologous polypeptide.

7. The fusion protein of claim 6 wherein the heterologous polypeptide is an enzyme.

8. A fusion protein comprising a chitin-binding polypeptide selected from the group consisting of polypeptides consisting of the sequence of amino acid residues X through Y of SEQ ID NO: 2, wherein X is a consecutive integer from 392 through 397 and Y is 445, and wherein said chitin-binding polypeptide is fused to a heterologous polypeptide.

9. A fusion protein comprising the polypeptide of any one of claims 2, 1, 3, 4 or 5 fused to a heterologous polypeptide.

10. The polypeptide or protein of claim 2, 8, 6 or 1 conjugated to an anti-fungal agent.

11. The polypeptide or protein of claim 10 wherein said anti-fungal agent is a fungicidal agent.

12. The polypeptide or protein of claim 10 wherein said anti-fungal agent is a fungistatic agent.

13. The polypeptide or protein of claim 10 wherein said anti-fungal agent is selected from the group consisting of amphotericin B, nystatin, pimaricin, 5-fluorocytosine, fluconazole, ketoconazole, clotrimazole, miconazole, econazole, butoconazole, oxiconazole, sulconazole, terconazole, itraconazole, tioconazole and other azole derivatives, tolnaftate, naftifine, terbinafine, and other allylamines-thiocarbamates, griseofulvin, ciclopirox olamine, haloprogin, undecylenic acid, and benzoic acid.

14. The polypeptide or protein of claim 10 wherein said anti-fungal agent is amphotericin B.

15. The polypeptide or protein of claim 10 wherein said anti-fungal agent is covalently bound to said polypeptide through an NHS linkage to a free amine at the N-terminus of said polypeptide.

16. The polypeptide or protein of claim 10 wherein said anti-fungal agent is covalently bound to said polypeptide through an NHS linkage to a free amine on a Lysine within said polypeptide.

17. The polypeptide or protein of claim 10 wherein said anti-fungal agent is covalently bound to said polypeptide through a succinimidyl linkage.

18. A composition comprising the polypeptide or protein of claim 2, 8, 6 or 1 and a physiologically acceptable diluent.

19. The composition of claim 18 further comprising a non-chitinase anti-fungal agent.

20. A composition comprising the polypeptide or protein of claim 2, 8, 6 or 1 conjugated to an anti-fungal agent.

21. The composition of claim 20 wherein said anti-fungal agent is selected from the group consisting of amphotericin B, nystatin, piniaricin, 5-fluorocytosine, fluconazole, ketoconazole, clotrimazole, miconazole, econazole, butoconazole, oxiconazole, sulconazole, terconazole, itraconazole, tioconazole and other azole derivatives, tolnaftate, naftifine, terbinafine, and other allylamines-thiocarbamates, griseofulvin, ciclopirox olamine, haloprogin, undecylenic acid, and benzoic acid.

22. The composition of claim 20 wherein said anti-fungal agent is amphotericin B.

23. A method of treating fungal infection comprising the step of administering to a subject suffering from fungal infection a composition according to any one of claims 19, 20, 10 or 12.

24. The method of claim 23 further comprising the step of administering to said subject a non-chitinase anti-fungal agent.

* * * * *

UNITED STATES PATENT AND TRADEMARK OFFICE
CERTIFICATE OF CORRECTION

PATENT NO. : 6,399,571 B1
DATED : June 4, 2002
INVENTOR(S) : Patrick W. Gray et al.

It is certified that error appears in the above-identified patent and that said Letters Patent is hereby corrected as shown below:

<u>Column 8,</u>
Line 14, replace "especially.humans" with -- especially humans --.
Line 45, replace "terbinafme" with -- terbinafine --.

<u>Column 9,</u>
Line 51, replace "TNP-α" with -- TNF-α --.

<u>Column 12,</u>
Line 33, replace "AGATCTAACCIT" with -- AGATCTAACCTT --.
Line 54, replace "arab-i" with -- arab-1 --.
Line 56, replace "TACAGAA" with -- TACAGAATTC --.
Line 63, replace "xbal" with -- Xbal --.

<u>Column 15,</u>
Line 3, replace "TCCGTrCC" with -- TCCGTTCC --.
Line 3, move "GGTCTGTGGCCTGGG," from line 3 to line 4.

<u>Column 16,</u>
Line 29, replace "2 nm" with -- 20 nM --.

<u>Column 21,</u>
Line 30, replace "CBDA" with -- CBDα --.
Line 43, replace "3°C" with -- 30°C --.

<u>Column 22,</u>
Line 27, replace "fmal" with -- final --.
Line 55, replace "15% PBS" with -- 15% FBS --.
Line 58, replace "10° Corning" with -- 10 Corning --.

<u>Column 25,</u>
Line 32, replace "EXAMPLE SA" with -- EXAMPLE 5A --.

<u>Column 26,</u>
Line 30, replace "5'10$^4$" with -- 5 x 10$^4$ --.

UNITED STATES PATENT AND TRADEMARK OFFICE
CERTIFICATE OF CORRECTION

PATENT NO. : 6,399,571 B1
DATED : June 4, 2002
INVENTOR(S) : Patrick W. Gray et al.

It is certified that error appears in the above-identified patent and that said Letters Patent is hereby corrected as shown below:

Column 30,
Line 18, replace "and the m position" with -- and the position --.
Line 60, replace "One hundred A1" with -- One hundred µl --.

Column 31, lines 41-67; Column 32, lines 41-67; Columns 33-54; Column 55, lines 1-29 and Column 56, lines 1-29, in the sequence listing, misalignment of codon triplicates and nucleotide decades throughout the listing due to insertion of extra space.

Signed and Sealed this

Second Day of September, 2003

JAMES E. ROGAN
*Director of the United States Patent and Trademark Office*

SEQUENCE LISTING

```
<160> NUMBER OF SEQ ID NOS: 39

<210> SEQ ID NO 1
<211> LENGTH: 1636
<212> TYPE: DNA
<213> ORGANISM: Homo sapiens
<220> FEATURE:
<221> NAME/KEY: CDS
<222> LOCATION: (2)..(1399)
<220> FEATURE:
<221> NAME/KEY: mat_peptide
<222> LOCATION: (65)..(1399)

<400> SEQUENCE: 1 c atg gtg cgg tct gtg gcc tgg gca ggt ttc  atg gtc ctg ctg atg atc     49
  Met Val Arg Ser Val Ala Trp Ala Gly Phe Met Val Leu Leu Met Ile
      -20              -15                  -10
cca tgg ggc tct gct gca aaa ctg gtc tgc t ac ttc acc aac tgg gcc        97
Pro Trp Gly Ser Ala Ala Lys Leu Val Cys T yr Phe Thr Asn Trp Ala
 -5              -1   1                5                      10
cag tac aga cag ggg gag gct cgc ttc ctg c cc aag gac ttg gac ccc       145
Gln Tyr Arg Gln Gly Glu Ala Arg Phe Leu P ro Lys Asp Leu Asp Pro
             15                  20                 25
agc ctt tgc acc cac ctc atc tac gcc ttc g ct ggc atg acc aac cac       193
```

-continued

```
Ser Leu Cys Thr His Leu Ile Tyr Ala Phe Ala Gly Met Thr Asn His
         30                  35                  40
cag ctg agc acc act gag tgg aat gac gag a ct ctc tac cag gag ttc      241
Gln Leu Ser Thr Thr Glu Trp Asn Asp Glu T hr Leu Tyr Gln Glu Phe
         45                  50                  55
aat ggc ctg aag aag atg aat ccc aag ctg a ag acc ctg tta gcc atc      289
Asn Gly Leu Lys Lys Met Asn Pro Lys Leu L ys Thr Leu Leu Ala Ile
60                  65                  70                  75
gga ggc tgg aat ttc ggc act cag aag ttc a ca gat atg gta gcc acg      337
Gly Gly Trp Asn Phe Gly Thr Gln Lys Phe T hr Asp Met Val Ala Thr
                 80                  85                  90
gcc aac aac cgt cag acc ttt gtc aac tcg g cc atc agg ttt ctg cgc      385
Ala Asn Asn Arg Gln Thr Phe Val Asn Ser A la Ile Arg Phe Leu Arg
             95                 100                 105
aaa tac agc ttt gac ggc ctt gac ctt gac t gg gag tac cca gga agc      433
Lys Tyr Ser Phe Asp Gly Leu Asp Leu Asp T rp Glu Tyr Pro Gly Ser
        110                 115                 120
cag ggg agc cct gcc gta gac aag gag cgc t tc aca acc ctg gta cag      481
Gln Gly Ser Pro Ala Val Asp Lys Glu Arg P he Thr Thr Leu Val Gln
    125                 130                 135
gac ttg gcc aat gcc ttc cag cag gaa gcc c ag acc tca ggg aag gaa      529
Asp Leu Ala Asn Ala Phe Gln Gln Glu Ala G ln Thr Ser Gly Lys Glu
140                 145                 150                 155
cgc ctt ctt ctg agt gca gcg gtt cca gct g gg cag acc tat gtg gat      577
Arg Leu Leu Leu Ser Ala Ala Val Pro Ala G ly Gln Thr Tyr Val Asp
                160                 165                 170
gct gga tac gag gtg gac aaa atc gcc cag a ac ctg gat ttt gtc aac      625
Ala Gly Tyr Glu Val Asp Lys Ile Ala Gln A sn Leu Asp Phe Val Asn
            175                 180                 185
ctt atg gcc tac gac ttc cat ggc tct tgg g ag aag gtc acg gga cat      673
Leu Met Ala Tyr Asp Phe His Gly Ser Trp G lu Lys Val Thr Gly His
        190                 195                 200
aac agc ccc ctc tac aag agg caa gaa gag a gt ggt gca gca gcc agc      721
Asn Ser Pro Leu Tyr Lys Arg Gln Glu Glu S er Gly Ala Ala Ala Ser
    205                 210                 215
ctc aac gtg gat gct gct gtg caa cag tgg c tg cag aag ggg acc cct      769
Leu Asn Val Asp Ala Ala Val Gln Gln Trp L eu Gln Lys Gly Thr Pro
220                 225                 230                 235
gcc agc aag ctg atc ctt ggc atg cct acc t ac gga cgc tcc ttc aca      817
Ala Ser Lys Leu Ile Leu Gly Met Pro Thr T yr Gly Arg Ser Phe Thr
                240                 245                 250
ctg gcc tcc tca tca gac acc aga gtg ggg g cc cca gcc aca ggg tct      865
Leu Ala Ser Ser Ser Asp Thr Arg Val Gly A la Pro Ala Thr Gly Ser
            255                 260                 265
ggc act cca ggc ccc ttc acc aag gaa gga g gg atg ctg gcc tac tat      913
Gly Thr Pro Gly Pro Phe Thr Lys Glu Gly G ly Met Leu Ala Tyr Tyr
        270                 275                 280
gaa gtc tgc tcc tgg aag ggg gcc acc aaa c ag aga atc cag gat cag      961
Glu Val Cys Ser Trp Lys Gly Ala Thr Lys G ln Arg Ile Gln Asp Gln
    285                 290                 295
aag gtg ccc tac atc ttc cgg gac aac cag t gg gtg ggc ttt gat gat     1009
Lys Val Pro Tyr Ile Phe Arg Asp Asn Gln T rp Val Gly Phe Asp Asp
300                 305                 310                 315
gtg gag agc ttc aaa acc aag gtc agc tat c tg aag cag aag gga ctg     1057
Val Glu Ser Phe Lys Thr Lys Val Ser Tyr L eu Lys Gln Lys Gly Leu
                320                 325                 330
ggc ggg gcc atg gtc tgg gca ctg gac tta g at gac ttt gcc ggc ttc     1105
Gly Gly Ala Met Val Trp Ala Leu Asp Leu A sp Asp Phe Ala Gly Phe
            335                 340                 345
tcc tgc aac cag ggc cga tac ccc ctc atc c ag acg cta cgg cag gaa     1153
Ser Cys Asn Gln Gly Arg Tyr Pro Leu Ile G ln Thr Leu Arg Gln Glu
        350                 355                 360
ctg agt ctt cca tac ttg cct tca ggc acc c ca gag ctt gaa gtt cca     1201
Leu Ser Leu Pro Tyr Leu Pro Ser Gly Thr P ro Glu Leu Glu Val Pro
    365                 370                 375
aaa cca ggt cag ccc tct gaa cct gag cat g gc ccc agc cct gga caa     1249
Lys Pro Gly Gln Pro Ser Glu Pro Glu His G ly Pro Ser Pro Gly Gln
380                 385                 390                 395
gac acg ttc tgc cag ggc aaa gct gat ggg c tc tat ccc aat cct cgg     1297
Asp Thr Phe Cys Gln Gly Lys Ala Asp Gly L eu Tyr Pro Asn Pro Arg
                400                 405                 410
gaa cgg tcc agc ttc tac agc tgt gca gcg g gg cgg ctg ttc cag caa     1345
Glu Arg Ser Ser Phe Tyr Ser Cys Ala Ala G ly Arg Leu Phe Gln Gln
            415                 420                 425
agc tgc ccg aca ggc ctg gtg ttc agc aac t cc tgc aaa tgc tgc acc     1393
Ser Cys Pro Thr Gly Leu Val Phe Ser Asn S er Cys Lys Cys Cys Thr
        430                 435                 440
tgg aat tgagtcgcta aagcccctcc agtcccagct tgaggctgg g cccaggatc      1449
Trp Asn
```

-continued

```
                445
actctacagc ctgcctcctg ggttttccct gggggccgca atctggctcc t gcaggcctt  1509
tctgtggtct tcctttatcc aggctttctg ctctcagcct tgccttcctt t tttctgggt  1569
ctcctgggct gccccttca cttgcaaaat aaatctttgg tttgtgcccc t cttcccaaa  1629
aaaaaaa                                                              1636
```

<210> SEQ ID NO 2
<211> LENGTH: 466
<212> TYPE: PRT
<213> ORGANISM: Homo sapiens

<400> SEQUENCE: 2

```
Met Val Arg Ser Val Ala Trp Ala Gly Phe M et Val Leu Leu Met Ile
        -20                 -15                 -10
Pro Trp Gly Ser Ala Ala Lys Leu Val Cys T yr Phe Thr Asn Trp Ala
 -5              -1   1               5                   10
Gln Tyr Arg Gln Gly Glu Ala Arg Phe Leu P ro Lys Asp Leu Asp Pro
             15                  20                  25
Ser Leu Cys Thr His Leu Ile Tyr Ala Phe A la Gly Met Thr Asn His
         30                  35                  40
Gln Leu Ser Thr Thr Glu Trp Asn Asp Glu T hr Leu Tyr Gln Glu Phe
     45                  50                  55
Asn Gly Leu Lys Lys Met Asn Pro Lys Leu L ys Thr Leu Leu Ala Ile
 60                  65                  70                  75
Gly Gly Trp Asn Phe Gly Thr Gln Lys Phe T hr Asp Met Val Ala Thr
                 80                  85                  90
Ala Asn Asn Arg Gln Thr Phe Val Asn Ser A la Ile Arg Phe Leu Arg
             95                 100                 105
Lys Tyr Ser Phe Asp Gly Leu Asp Leu Asp T rp Glu Tyr Pro Gly Ser
        110                 115                 120
Gln Gly Ser Pro Ala Val Asp Lys Glu Arg P he Thr Thr Leu Val Gln
    125                 130                 135
Asp Leu Ala Asn Ala Phe Gln Gln Glu Ala G ln Thr Ser Gly Lys Glu
140                 145                 150                 155
Arg Leu Leu Leu Ser Ala Ala Val Pro Ala G ly Gln Thr Tyr Val Asp
                160                 165                 170
Ala Gly Tyr Glu Val Asp Lys Ile Ala Gln A sn Leu Asp Phe Val Asn
            175                 180                 185
Leu Met Ala Tyr Asp Phe His Gly Ser Trp G lu Lys Val Thr Gly His
        190                 195                 200
Asn Ser Pro Leu Tyr Lys Arg Gln Glu Glu S er Gly Ala Ala Ala Ser
    205                 210                 215
Leu Asn Val Asp Ala Ala Val Gln Gln Trp L eu Gln Lys Gly Thr Pro
220                 225                 230                 235
Ala Ser Lys Leu Ile Leu Gly Met Pro Thr T yr Gly Arg Ser Phe Thr
                240                 245                 250
Leu Ala Ser Ser Ser Asp Thr Arg Val Gly A la Pro Ala Thr Gly Ser
            255                 260                 265
Gly Thr Pro Gly Pro Phe Thr Lys Glu Gly G ly Met Leu Ala Tyr Tyr
        270                 275                 280
Glu Val Cys Ser Trp Lys Gly Ala Thr Lys G ln Arg Ile Gln Asp Gln
    285                 290                 295
Lys Val Pro Tyr Ile Phe Arg Asp Asn Gln T rp Val Gly Phe Asp Asp
300                 305                 310                 315
Val Glu Ser Phe Lys Thr Lys Val Ser Tyr L eu Lys Gln Lys Gly Leu
                320                 325                 330
Gly Gly Ala Met Val Trp Ala Leu Asp Leu A sp Asp Phe Ala Gly Phe
            335                 340                 345
Ser Cys Asn Gln Gly Arg Tyr Pro Leu Ile G ln Thr Leu Arg Gln Glu
        350                 355                 360
Leu Ser Leu Pro Tyr Leu Pro Ser Gly Thr P ro Glu Leu Glu Val Pro
    365                 370                 375
Lys Pro Gly Gln Pro Ser Glu Pro Glu His G ly Pro Ser Pro Gly Gln
380                 385                 390                 395
Asp Thr Phe Cys Gln Gly Lys Ala Asp Gly L eu Tyr Pro Asn Pro Arg
                400                 405                 410
Glu Arg Ser Ser Phe Tyr Ser Cys Ala Ala G ly Arg Leu Phe Gln Gln
            415                 420                 425
Ser Cys Pro Thr Gly Leu Val Phe Ser Asn S er Cys Lys Cys Cys Thr
        430                 435                 440
Trp Asn
    445
```

<210> SEQ ID NO 3
<211> LENGTH: 1656
<212> TYPE: DNA

```
<213> ORGANISM: Homo sapiens
<220> FEATURE:
<221> NAME/KEY: CDS
<222> LOCATION: (27)..(1424)
<220> FEATURE:
<221> NAME/KEY: mat_peptide
<222> LOCATION: (90)..(1424)

<400> SEQUENCE: 3
gctgcagcct gccgctgagc tgcatc atg gtg cgg tct gtg gcc tgg gca ggt        53
                              Met Val Arg Ser Val Ala Trp Ala Gly
                                  -20                 -15 ttc atg gtc ctg ctg atg atc cca tgg ggc t ct gct gca aaa ctg gtc       101
Phe Met Val Leu Leu Met Ile Pro Trp Gly S er Ala Ala Lys Leu Val
        -10              -5                 -1  1 tgc tac ttc acc aac tgg gcc cag tac aga c ag ggg gag gct cgc ttc       149
Cys Tyr Phe Thr Asn Trp Ala Gln Tyr Arg G ln Gly Glu Ala Arg Phe
 5                  10                 15                  20 ctg ccc aag gac ttg gac ccc agc ctt tgc a cc cac ctc atc tac gcc       197
Leu Pro Lys Asp Leu Asp Pro Ser Leu Cys T hr His Leu Ile Tyr Ala
             25                  30                  35 ttc gct ggc atg acc aac cac cag ctg agc a cc act gag tgg aat gac       245
Phe Ala Gly Met Thr Asn His Gln Leu Ser T hr Thr Glu Trp Asn Asp
                 40                  45                  50 gag act ctc tac cag gag ttc aat ggc ctg a ag aag atg aat ccc aag       293
Glu Thr Leu Tyr Gln Glu Phe Asn Gly Leu L ys Lys Met Asn Pro Lys
             55                  60                  65 ctg aag acc ctg tta gcc atc gga ggc tgg a at ttc agc act cag aag       341
Leu Lys Thr Leu Leu Ala Ile Gly Gly Trp A sn Phe Ser Thr Gln Lys
 70                  75                  80 ttc aca gat atg gta gcc acg gcc aac aac c gt cag acc ttt gtc aac       389
Phe Thr Asp Met Val Ala Thr Ala Asn Asn A rg Gln Thr Phe Val Asn
 85                  90                  95                 100 tcg gcc atc agg ttt ctg cgc aaa tac agc t tt gac ggc ctt gac ctt       437
Ser Ala Ile Arg Phe Leu Arg Lys Tyr Ser P he Asp Gly Leu Asp Leu
                105                 110                 115 gac tgg gag tac cca gga agc cag ggg agc c ct gcc gta gac aag gag       485
Asp Trp Glu Tyr Pro Gly Ser Gln Gly Ser P ro Ala Val Asp Lys Glu
                120                 125                 130 cgc ttc aca acc ctg gta cag gac ttg gca a at gcc ttc cag cag gaa       533
Arg Phe Thr Thr Leu Val Gln Asp Leu Ala A sn Ala Phe Gln Gln Glu
                135                 140                 145 gcc cag acc tca ggg aag gaa cgc ctt ctt c tg agt gca gcg gtt cca       581
Ala Gln Thr Ser Gly Lys Glu Arg Leu Leu L eu Ser Ala Ala Val Pro
        150                 155                 160 gct ggg cag acc tat gtg gat gct gga tac g ag gtg gac aaa atc gcc       629
Ala Gly Gln Thr Tyr Val Asp Ala Gly Tyr G lu Val Asp Lys Ile Ala
165                 170                 175                 180 cag aac ctg gat ttt gtc aac ctt atg gcc t ac gac ttc cat ggc tct       677
Gln Asn Leu Asp Phe Val Asn Leu Met Ala T yr Asp Phe His Gly Ser
                185                 190                 195 tgg gag aag gtc acg gga cat aac agc ccc c tc tac aag agg caa gaa       725
Trp Glu Lys Val Thr Gly His Asn Ser Pro L eu Tyr Lys Arg Gln Glu
                200                 205                 210 gag agt ggt gca gca gcc agc ctc aac gtg g at gct gct gtg caa cag       773
Glu Ser Gly Ala Ala Ala Ser Leu Asn Val A sp Ala Ala Val Gln Gln
        215                 220                 225 tgg ctg cag aag ggg acc cct gcc agc aag c tg atc ctt ggc atg cct       821
Trp Leu Gln Lys Gly Thr Pro Ala Ser Lys L eu Ile Leu Gly Met Pro
        230                 235                 240 acc tac gga cgc tcc ttc aca ctg gcc tcc t ca tca gac acc aga gtg       869
Thr Tyr Gly Arg Ser Phe Thr Leu Ala Ser S er Ser Asp Thr Arg Val
245                 250                 255                 260 ggg gcc cca gcc aca ggg tct ggc act cca g gc ccc ttc acc aag gaa       917
Gly Ala Pro Ala Thr Gly Ser Gly Thr Pro G ly Pro Phe Thr Lys Glu
                265                 270                 275 gga ggg atg ctg gcc tac tat gaa gtc tgc t cc tgg aag ggg gcc acc       965
Gly Gly Met Leu Ala Tyr Tyr Glu Val Cys S er Trp Lys Gly Ala Thr
                280                 285                 290 aaa cag aga atc cag gat cag aag gtg ccc t ac atc ttc cgg gac aac      1013
Lys Gln Arg Ile Gln Asp Gln Lys Val Pro T yr Ile Phe Arg Asp Asn
        295                 300                 305 cag tgg gtg ggc ttt gat gat gtg gag agc t tc aaa acc aag gtc agc      1061
Gln Trp Val Gly Phe Asp Asp Val Glu Ser P he Lys Thr Lys Val Ser
        310                 315                 320 tat ctg aag cag aag gga ctg ggc ggg gcc a tg gtc tgg gca ctg gac      1109
Tyr Leu Lys Gln Lys Gly Leu Gly Gly Ala M et Val Trp Ala Leu Asp
325                 330                 335                 340
```

-continued

```
tta gat gac ttt gcc ggc ttc tcc tgc aac c ag ggc cga tac ccc ctc    1157
Leu Asp Asp Phe Ala Gly Phe Ser Cys Asn G ln Gly Arg Tyr Pro Leu
                345                     350                 355
atc cag acg cta cgg cag gaa ctg agt ctt c ca tac ttg cct tca ggc    1205
Ile Gln Thr Leu Arg Gln Glu Leu Ser Leu P ro Tyr Leu Pro Ser Gly
            360                 365                 370
acc cca gag ctt gaa gtt cca aaa cca ggt c ag ccc tct gaa cct gag    1253
Thr Pro Glu Leu Glu Val Pro Lys Pro Gly G ln Pro Ser Glu Pro Glu
        375                 380                 385
cat ggc ccc agc cct gga caa gac acg ttc t gc cag ggc aaa gct gat    1301
His Gly Pro Ser Pro Gly Gln Asp Thr Phe C ys Gln Gly Lys Ala Asp
    390                 395                 400
ggg ctc tat ccc aat cct cgg gaa cgg tcc a gc ttc tac agc tgt gca    1349
Gly Leu Tyr Pro Asn Pro Arg Glu Arg Ser S er Phe Tyr Ser Cys Ala
405                 410                 415                 420
gcg ggg cgg ctg ttc cag caa agc tgc ccg a ca ggc ctg gtg ttc agc    1397
Ala Gly Arg Leu Phe Gln Gln Ser Cys Pro T hr Gly Leu Val Phe Ser
                425                 430                 435
aac tcc tgc aaa tgc tgc acc tgg aat tgagtcgc ta aagcccctcc         1444
Asn Ser Cys Lys Cys Cys Thr Trp Asn
            440                 445
agtcccagct tgaggctgg gcccaggatc actctacagc ctgcctcctg g ttttccct    1504
gggggccgca atctggctcc tgcaggcctt tctgtggtct tcctttatcc a ggctttctg  1564
ctctcagcct tgccttcctt ttttctgggt ctcctgggct gccccttca c ttgcaaaat   1624
aaatctttgg tttgtgcccc tcaaaaaaaa aa                                 1656
```

<210> SEQ ID NO 4
<211> LENGTH: 466
<212> TYPE: PRT
<213> ORGANISM: Homo sapiens

<400> SEQUENCE: 4

```
Met Val Arg Ser Val Ala Trp Ala Gly Phe M et Val Leu Leu Met Ile
-20                     -15                     -10
Pro Trp Gly Ser Ala Ala Lys Leu Val Cys T yr Phe Thr Asn Trp Ala
 -5              -1  1                   5                   10
Gln Tyr Arg Gln Gly Glu Ala Arg Phe Leu P ro Lys Asp Leu Asp Pro
                 15                  20                  25
Ser Leu Cys Thr His Leu Ile Tyr Ala Phe A la Gly Met Thr Asn His
             30                  35                  40
Gln Leu Ser Thr Thr Glu Trp Asn Asp Glu T hr Leu Tyr Gln Glu Phe
         45                  50                  55
Asn Gly Leu Lys Lys Met Asn Pro Lys Leu L ys Thr Leu Leu Ala Ile
 60                  65                  70                  75
Gly Gly Trp Asn Phe Ser Thr Gln Lys Phe T hr Asp Met Val Ala Thr
                 80                  85                  90
Ala Asn Asn Arg Gln Thr Phe Val Asn Ser A la Ile Arg Phe Leu Arg
             95                  100                 105
Lys Tyr Ser Phe Asp Gly Leu Asp Leu Asp T rp Glu Tyr Pro Gly Ser
        110                 115                 120
Gln Gly Ser Pro Ala Val Asp Lys Glu Arg P he Thr Thr Leu Val Gln
    125                 130                 135
Asp Leu Ala Asn Ala Phe Gln Gln Glu Ala G ln Thr Ser Gly Lys Glu
140                 145                 150                 155
Arg Leu Leu Leu Ser Ala Val Pro Ala Gly G ln Thr Tyr Val Asp
                160                 165                 170
Ala Gly Tyr Glu Val Asp Lys Ile Ala Gln A sn Leu Asp Phe Val Asn
            175                 180                 185
Leu Met Ala Tyr Asp Phe His Gly Ser Trp G lu Lys Val Thr Gly His
        190                 195                 200
Asn Ser Pro Leu Tyr Lys Arg Gln Glu Glu S er Gly Ala Ala Ala Ser
    205                 210                 215
Leu Asn Val Asp Ala Ala Val Gln Gln Trp L eu Gln Lys Gly Thr Pro
220                 225                 230                 235
Ala Ser Lys Leu Ile Leu Gly Met Pro Thr T yr Gly Arg Ser Phe Thr
                240                 245                 250
Leu Ala Ser Ser Ser Asp Thr Arg Val Gly A la Pro Ala Thr Gly Ser
            255                 260                 265
Gly Thr Pro Gly Pro Phe Thr Lys Glu Gly G ly Met Leu Ala Tyr Tyr
        270                 275                 280
Glu Val Cys Ser Trp Lys Gly Ala Thr Lys G ln Arg Ile Gln Asp Gln
    285                 290                 295
Lys Val Pro Tyr Ile Phe Arg Asp Asn Gln T rp Val Gly Phe Asp Asp
300                 305                 310                 315
Val Glu Ser Phe Lys Thr Lys Val Ser Tyr L eu Lys Gln Lys Gly Leu
                320                 325                 330
Gly Gly Ala Met Val Trp Ala Leu Asp Leu A sp Asp Phe Ala Gly Phe
```

-continued

```
              335                 340                 345
Ser Cys Asn Gln Gly Arg Tyr Pro Leu Ile Gln Thr Leu Arg Gln Glu
        350                 355                 360
Leu Ser Leu Pro Tyr Leu Pro Ser Gly Thr Pro Glu Leu Glu Val Pro
    365                 370                 375
Lys Pro Gly Gln Pro Ser Glu Pro Glu His Gly Pro Ser Pro Gly Gln
380                 385                 390                 395
Asp Thr Phe Cys Gln Gly Lys Ala Asp Gly Leu Tyr Pro Asn Pro Arg
                400                 405                 410
Glu Arg Ser Ser Phe Tyr Ser Cys Ala Ala Gly Arg Leu Phe Gln Gln
            415                 420                 425
Ser Cys Pro Thr Gly Leu Val Phe Ser Asn Ser Cys Lys Cys Cys Thr
        430                 435                 440
Trp Asn
    445
```

<210> SEQ ID NO 5
<211> LENGTH: 18
<212> TYPE: DNA
<213> ORGANISM: Artificial Sequence
<220> FEATURE:
<223> OTHER INFORMATION: Description of Artificial  Sequence: primer

<400> SEQUENCE: 5
gacactatag aatagggc                                           18

<210> SEQ ID NO 6
<211> LENGTH: 51
<212> TYPE: DNA
<213> ORGANISM: Artificial Sequence
<220> FEATURE:
<223> OTHER INFORMATION: Description of Artificial  Sequence: primer

<400> SEQUENCE: 6
tgggatcatc agcaggacca tgaaacctgc ccaggccaca gaccgcacca t       51

<210> SEQ ID NO 7
<211> LENGTH: 40
<212> TYPE: DNA
<213> ORGANISM: Artificial Sequence
<220> FEATURE:
<223> OTHER INFORMATION: Description of Artificial  Sequence: primer

<400> SEQUENCE: 7
tacatctaga attatggcaa aactggtctg ctacttcacc                   40

<210> SEQ ID NO 8
<211> LENGTH: 34
<212> TYPE: DNA
<213> ORGANISM: Artificial Sequence
<220> FEATURE:
<223> OTHER INFORMATION: Description of Artificial  Sequence: primer

<400> SEQUENCE: 8
agatctaacc ttaggtgcct gaagacaagt atgg                         34

<210> SEQ ID NO 9
<211> LENGTH: 29
<212> TYPE: DNA
<213> ORGANISM: Artificial Sequence
<220> FEATURE:
<223> OTHER INFORMATION: Description of Artificial  Sequence: primer

<400> SEQUENCE: 9
tacagaattc ttattcacat ccggccctg                               29

<210> SEQ ID NO 10
<211> LENGTH: 34

<212> TYPE: DNA
<213> ORGANISM: Artificial Sequence
<220> FEATURE:
<223> OTHER INFORMATION: Description of Artificial Sequence: primer

<400> SEQUENCE: 10
tacatctaga ctccatccag aaaaacaggt atgg            34

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 11
tctagagtcg acctgcaggc atgcaagctt            30

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 12
cgcaagcttg agagctccgt tccgccacat ggtgcggtct gtggcctggg            50

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 13
gactctagac taggtgcctg aaggcaagta tg            32

<210> SEQ ID NO 14
<211> LENGTH: 373
<212> TYPE: PRT
<213> ORGANISM: Homo sapiens

<400> SEQUENCE: 14

Ala Lys Leu Val Cys Tyr Phe Thr Asn Trp Ala Gln Tyr Arg Gln Gly
 1               5                  10                  15

Glu Ala Arg Phe Leu Pro Lys Asp Leu Asp Pro Ser Leu Cys Thr His
            20                  25                  30

Leu Ile Tyr Ala Phe Ala Gly Met Thr Asn His Gln Leu Ser Thr Thr
        35                  40                  45

Glu Trp Asn Asp Glu Thr Leu Tyr Gln Glu Phe Asn Gly Leu Lys Lys
    50                  55                  60

Met Asn Pro Lys Leu Lys Thr Leu Leu Ala Ile Gly Gly Trp Asn Phe
65                  70                  75                  80

Gly Thr Gln Lys Phe Thr Asp Met Val Ala Thr Ala Asn Asn Arg Gln
                85                  90                  95

Thr Phe Val Asn Ser Ala Ile Arg Phe Leu Arg Lys Tyr Ser Phe Asp
            100                 105                 110

Gly Leu Asp Leu Asp Trp Glu Tyr Pro Gly Ser Gln Gly Ser Pro Ala
        115                 120                 125

Val Asp Lys Glu Arg Phe Thr Thr Leu Val Gln Asp Leu Ala Asn Ala
    130                 135                 140

Phe Gln Gln Glu Ala Gln Thr Ser Gly Lys Glu Arg Leu Leu Leu Ser
145                 150                 155                 160

Ala Ala Val Pro Ala Gly Gln Thr Tyr Val Asp Ala Gly Tyr Glu Val
                165                 170                 175

Asp Lys Ile Ala Gln Asn Leu Asp Phe Val Asn Leu Met Ala Tyr Asp
            180                 185                 190

Phe His Gly Ser Trp Glu Lys Val Thr Gly His Asn Ser Pro Leu Tyr
        195                 200                 205

Lys Arg Gln Glu Glu Ser Gly Ala Ala Ser Leu Asn Val Asp Ala
    210                 215                 220

Ala Val Gln Gln Trp Leu Gln Lys Gly Thr Pro Ala Ser Lys Leu Ile
225                 230                 235                 240

Leu Gly Met Pro Thr Tyr Gly Arg Ser Phe Thr Leu Ala Ser Ser Ser
                245                 250                 255

Asp Thr Arg Val Gly Ala Pro Ala Thr Gly Ser Gly Thr Pro Gly Pro
                260                 265                 270

Phe Thr Lys Glu Gly Gly Met Leu Ala Tyr Tyr Glu Val Cys Ser Trp
            275                 280                 285

Lys Gly Ala Thr Lys Gln Arg Ile Gln Asp Gln Lys Val Pro Tyr Ile
    290                 295                 300

Phe Arg Asp Asn Gln Trp Val Gly Phe Asp Asp Val Glu Ser Phe Lys
305                 310                 315                 320

Thr Lys Val Ser Tyr Leu Lys Gln Lys Gly Leu Gly Gly Ala Met Val
                325                 330                 335

Trp Ala Leu Asp Leu Asp Asp Phe Ala Gly Phe Ser Cys Asn Gln Gly
                340                 345                 350

Arg Tyr Pro Leu Ile Gln Thr Leu Arg Gln Glu Leu Ser Leu Pro Tyr
            355                 360                 365

Leu Pro Ser Gly Thr
            370

<210> SEQ ID NO 15
<211> LENGTH: 373
<212> TYPE: PRT
<213> ORGANISM: Homo sapiens

<400> SEQUENCE: 15

Ala Lys Leu Val Cys Tyr Phe Thr Asn Trp Ala Gln Tyr Arg Gln Gly
1               5                   10                  15

Glu Ala Arg Phe Leu Pro Lys Asp Leu Asp Pro Ser Leu Cys Thr His
            20                  25                  30

Leu Ile Tyr Ala Phe Ala Gly Met Thr Asn His Gln Leu Ser Thr Thr
        35                  40                  45

Glu Trp Asn Asp Glu Thr Leu Tyr Gln Glu Phe Asn Gly Leu Lys Lys
    50                  55                  60

Met Asn Pro Lys Leu Lys Thr Leu Leu Ala Ile Gly Gly Trp Asn Phe
65                  70                  75                  80

Gly Thr Gln Lys Phe Thr Asp Met Val Ala Thr Ala Asn Asn Arg Gln
                85                  90                  95

Thr Phe Val Asn Ser Ala Ile Arg Phe Leu Arg Lys Tyr Ser Phe Asp
            100                 105                 110

Gly Leu Asp Leu Asp Trp Glu Tyr Pro Gly Ser Gln Gly Ser Pro Ala
        115                 120                 125

Val Asp Lys Glu Arg Phe Thr Thr Leu Val Gln Asp Leu Ala Asn Ala

```
            130                 135                 140
Phe Gln Gln Glu Ala Gln Thr Ser Gly Lys Glu Arg Leu Leu Leu Ser
145                 150                 155                 160
Ala Ala Val Pro Ala Gly Gln Thr Tyr Val Asp Ala Gly Tyr Glu Val
                165                 170                 175
Asp Lys Ile Ala Gln Asn Leu Asp Phe Val Asn Leu Met Ala Tyr Asp
            180                 185                 190
Phe His Gly Ser Trp Glu Lys Val Thr Gly His Asn Ser Pro Leu Tyr
        195                 200                 205
Lys Arg Gln Glu Glu Ser Gly Ala Ala Ala Ser Leu Asn Val Asp Ala
    210                 215                 220
Ala Val Gln Gln Trp Leu Gln Lys Gly Thr Pro Ala Ser Lys Leu Ile
225                 230                 235                 240
Leu Gly Met Pro Thr Tyr Gly Arg Ser Phe Thr Leu Ala Ser Ser Ser
                245                 250                 255
Asp Thr Arg Val Gly Ala Pro Ala Thr Gly Ser Gly Thr Pro Gly Pro
            260                 265                 270
Phe Thr Lys Glu Gly Gly Met Leu Ala Tyr Tyr Glu Val Cys Ser Trp
        275                 280                 285
Lys Gly Ala Thr Lys Gln Arg Ile Gln Asp Gln Lys Val Pro Tyr Ile
    290                 295                 300
Phe Arg Asp Asn Gln Trp Val Gly Phe Asp Asp Val Glu Ser Phe Lys
305                 310                 315                 320
Thr Lys Val Ser Tyr Leu Lys Gln Lys Gly Leu Gly Gly Ala Met Val
                325                 330                 335
Trp Ala Leu Asp Leu Asp Asp Phe Ala Gly Phe Ser Cys Asn Gln Gly
            340                 345                 350
Arg Tyr Pro Leu Ile Gln Thr Leu Arg Gln Glu Leu Ser Leu Pro Tyr
        355                 360                 365
Leu Ser Ser Gly Thr
    370

<210> SEQ ID NO 16
<211> LENGTH: 28
<212> TYPE: DNA
<213> ORGANISM: Artificial Sequence
<220> FEATURE:
<223> OTHER INFORMATION: Description of Artificial  Sequence: primer

<400> SEQUENCE: 16
tgatacggta ccgccccatg gctgacta                                   28

<210> SEQ ID NO 17
<211> LENGTH: 20
<212> TYPE: DNA
<213> ORGANISM: Artificial Sequence
<220> FEATURE:
<223> OTHER INFORMATION: Description of Artificial  Sequence: primer

<400> SEQUENCE: 17
gcaagtttgg cgcgaaatcg                                            20

<210> SEQ ID NO 18
<211> LENGTH: 66
<212> TYPE: DNA
<213> ORGANISM: Artificial Sequence
<220> FEATURE:
<223> OTHER INFORMATION: Description of Artificial  Sequence: primer
```

-continued

```
<400> SEQUENCE: 18
gcttaagctt gctgcagcct gccgctgagc tgcatcatgc tactactact g ctgctgctg      60 ggcctg                                                                 66

<210> SEQ ID NO 19
<211> LENGTH: 115
<212> TYPE: DNA
<213> ORGANISM: Artificial Sequence
<220> FEATURE:
<223> OTHER INFORMATION: Description of Artificial  Sequence: primer

<400> SEQUENCE: 19
aacagggccc ttaattaatt aggtacctgc gcggccgcag catcgattgc t ctagaagcg      60 atatcagcga attctgtctg ctcgaagcgg ccggccgccc cgactcgaga g taac          115

<210> SEQ ID NO 20
<211> LENGTH: 34
<212> TYPE: DNA
<213> ORGANISM: Artificial Sequence
<220> FEATURE:
<223> OTHER INFORMATION: Description of Artificial  Sequence: primer

<400> SEQUENCE: 20
tatagaattc ttctcctgca accagggccg atac                                  34

<210> SEQ ID NO 21
<211> LENGTH: 35
<212> TYPE: DNA
<213> ORGANISM: Artificial Sequence
<220> FEATURE:
<223> OTHER INFORMATION: Description of Artificial  Sequence: primer

<400> SEQUENCE: 21
tatagaattc ccagagcttg aagttccaaa accag                                 35

<210> SEQ ID NO 22
<211> LENGTH: 35
<212> TYPE: DNA
<213> ORGANISM: Artificial Sequence
<220> FEATURE:
<223> OTHER INFORMATION: Description of Artificial  Sequence: primer

<400> SEQUENCE: 22
tatagaattc agccctggac aagacacgtt ctgcc                                 35

<210> SEQ ID NO 23
<211> LENGTH: 35
<212> TYPE: DNA
<213> ORGANISM: Artificial Sequence
<220> FEATURE:
<223> OTHER INFORMATION: Description of Artificial  Sequence: primer

<400> SEQUENCE: 23
agaggaattc cagggcaaag ctgatgggct ctatc                                 35

<210> SEQ ID NO 24
<211> LENGTH: 37
<212> TYPE: DNA
<213> ORGANISM: Artificial Sequence
<220> FEATURE:
<223> OTHER INFORMATION: Description of Artificial  Sequence: primer

<400> SEQUENCE: 24
acaggaattc aatcctcggg aacggtccag cttctac                               37
```

-continued

<210> SEQ ID NO 25
<211> LENGTH: 37
<212> TYPE: DNA
<213> ORGANISM: Artificial Sequence
<220> FEATURE:
<223> OTHER INFORMATION: Description of Artificial  Sequence: primer

<400> SEQUENCE: 25
cacatctaga ttatgtcggg cagctttgct ggaacag                                37

<210> SEQ ID NO 26
<211> LENGTH: 36
<212> TYPE: DNA
<213> ORGANISM: Artificial Sequence
<220> FEATURE:
<223> OTHER INFORMATION: Description of Artificial  Sequence: primer

<400> SEQUENCE: 26
agagtctaga tcaattccag gtgcagcatt tgcagg                                 36

<210> SEQ ID NO 27
<211> LENGTH: 35
<212> TYPE: DNA
<213> ORGANISM: Artificial Sequence
<220> FEATURE:
<223> OTHER INFORMATION: Description of Artificial  Sequence: primer

<400> SEQUENCE: 27
agaggaattc agccctggac aagacacgtt cagcc                                  35

<210> SEQ ID NO 28
<211> LENGTH: 97
<212> TYPE: DNA
<213> ORGANISM: Artificial Sequence
<220> FEATURE:
<223> OTHER INFORMATION: Description of Artificial  Sequence: primer

<400> SEQUENCE: 28
agaggaattc agccctggac aagacacgtt ctgccagggc aaagctgatg g gctctatcc      60 caatcctcgg gaacggtcca gcttctacag cagtgca                                97

<210> SEQ ID NO 29
<211> LENGTH: 67
<212> TYPE: DNA
<213> ORGANISM: Artificial Sequence
<220> FEATURE:
<223> OTHER INFORMATION: Description of Artificial  Sequence: primer

<400> SEQUENCE: 29
tgcttctaga ttaattccag gtgcagcatt tgcaggagtt gctgaacacc a ggcctgtcg      60 ggctgct                                                                 67

<210> SEQ ID NO 30
<211> LENGTH: 36
<212> TYPE: DNA
<213> ORGANISM: Artificial Sequence
<220> FEATURE:
<223> OTHER INFORMATION: Description of Artificial  Sequence: primer

<400> SEQUENCE: 30
tgcttctaga ttaattccag gtgcagcatt tgctgg                                 36

<210> SEQ ID NO 31

```
<211> LENGTH: 36
<212> TYPE: DNA
<213> ORGANISM: Artificial Sequence
<220> FEATURE:
<223> OTHER INFORMATION: Description of Artificial  Sequence: primer

<400> SEQUENCE: 31
tgcttctaga ttaattccag gtgcagcttt tgcagg                               36

<210> SEQ ID NO 32
<211> LENGTH: 36
<212> TYPE: DNA
<213> ORGANISM: Artificial Sequence
<220> FEATURE:
<223> OTHER INFORMATION: Description of Artificial  Sequence: primer

<400> SEQUENCE: 32
tgcttctaga ttaattccag gtgctgcatt tgcagg                               36

<210> SEQ ID NO 33
<211> LENGTH: 72
<212> TYPE: DNA
<213> ORGANISM: Artificial Sequence
<220> FEATURE:
<223> OTHER INFORMATION: Description of Artificial  Sequence: primer

<400> SEQUENCE: 33
ctctggtacc tttggataaa agagactaca aggacgacga tgacaagagc c ctggacaag    60 acacgttctg cc                                                         72

<210> SEQ ID NO 34
<211> LENGTH: 77
<212> TYPE: DNA
<213> ORGANISM: Artificial Sequence
<220> FEATURE:
<223> OTHER INFORMATION: Description of Artificial  Sequence: primer

<400> SEQUENCE: 34
atatgcggcc gcgacttatc cactactatg atgatgatga tgatgtcctg c tccattcca    60 ggtgcagcat ttgcagg                                                    77

<210> SEQ ID NO 35
<211> LENGTH: 37
<212> TYPE: DNA
<213> ORGANISM: Artificial Sequence
<220> FEATURE:
<223> OTHER INFORMATION: Description of Artificial  Sequence: primer

<400> SEQUENCE: 35
ctctgaattc caagacacgt tctgccaggg caaagct                              37

<210> SEQ ID NO 36
<211> LENGTH: 35
<212> TYPE: DNA
<213> ORGANISM: Artificial Sequence
<220> FEATURE:
<223> OTHER INFORMATION: Description of Artificial  Sequence: primer

<400> SEQUENCE: 36
atatgaattc acgttctgcc agggcaaagc tgatg                                35

<210> SEQ ID NO 37
<211> LENGTH: 41
<212> TYPE: DNA
<213> ORGANISM: Artificial Sequence
```

-continued

```
<220> FEATURE:
<223> OTHER INFORMATION: Description of Artificial  Sequence: primer

<400> SEQUENCE: 37
aacatctaga ttaggtgcag catttgcagg agttgctgaa c                         41

<210> SEQ ID NO 38
<211> LENGTH: 48
<212> TYPE: DNA
<213> ORGANISM: Artificial Sequence
<220> FEATURE:
<223> OTHER INFORMATION: Description of Artificial  Sequence: primer

<400> SEQUENCE: 38
aagaggtacc tttggataaa agaagccctg gacaagacac gttctgcc                  48

<210> SEQ ID NO 39
<211> LENGTH: 41
<212> TYPE: DNA
<213> ORGANISM: Artificial Sequence
<220> FEATURE:
<223> OTHER INFORMATION: Description of Artificial  Sequence: primer

<400> SEQUENCE: 39
gagagcggcc gcgacttaat tccaggtgca gcatttgcag g                         41
```